United States Patent
Schelwies et al.

(10) Patent No.: US 11,708,316 B2
(45) Date of Patent: Jul. 25, 2023

(54) HYDROGENATION OF ESTERS TO ALCOHOLS IN THE PRESENCE OF A RU-PNN COMPLEX

(71) Applicant: BASF SE, Ludwigshafen am Rhein (DE)

(72) Inventors: Mathias Schelwies, Ludwigshafen am Rhein (DE); Jonas Schwaben, Ludwigshafen am Rhein (DE); Rocco Paciello, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/623,642

(22) PCT Filed: Jun. 24, 2020

(86) PCT No.: PCT/EP2020/067683
§ 371 (c)(1),
(2) Date: Dec. 29, 2021

(87) PCT Pub. No.: WO2021/001240
PCT Pub. Date: Jan. 7, 2021

(65) Prior Publication Data
US 2022/0380279 A1  Dec. 1, 2022

(30) Foreign Application Priority Data
Jul. 3, 2019 (EP) .................................... 19184178
Apr. 29, 2020 (EP) .................................... 20171976

(51) Int. Cl.
C07C 41/26 (2006.01)
C07C 29/149 (2006.01)
C07C 29/156 (2006.01)

(52) U.S. Cl.
CPC ............ *C07C 41/26* (2013.01); *C07C 29/149* (2013.01); *C07C 29/156* (2013.01); *C07C 2602/28* (2017.05)

(58) Field of Classification Search
None
See application file for complete search history.

(56) References Cited

U.S. PATENT DOCUMENTS

| | | | |
|---|---|---|---|
| 7,989,665 B2 | 8/2011 | Saudan et al. | |
| 8,013,193 B2 | 9/2011 | Maeda et al. | |
| 8,124,816 B2 | 2/2012 | Saudan et al. | |
| 8,178,723 B2 | 5/2012 | Milstein et al. | |
| 8,471,048 B2 | 6/2013 | Kuriyama et al. | |
| 8,524,953 B2 | 9/2013 | Kuriyama et al. | |
| 9,193,651 B2 | 11/2015 | Geisser et al. | |
| 2014/0328748 A1 | 11/2014 | Goussev et al. | |
| 2017/0283447 A1 | 10/2017 | Milstein et al. | |

FOREIGN PATENT DOCUMENTS

| | | | |
|---|---|---|---|
| WO | 2012/052996 A2 | 4/2012 | |
| WO | 2013/023307 A1 | 2/2013 | |
| WO | 2017/134618 A1 | 8/2017 | |
| WO | WO-2019175158 A1 * | 9/2019 | ............ B01J 31/189 |

OTHER PUBLICATIONS

Fujii, et al., "Ruthenium(II)-Catalyzed Asymmetric Transfer Hydrogenation of Ketones Using a Formic Acid-Triethylamine Mixture", Journal of the American Chemical Society, vol. 118, Issue 10, 1996, pp. 2521-2522.
International Preliminary Report on Patentability received for PCT Patent Application No. PCT/EP2020/067683, dated Jan. 13, 2022, 14 pages (8 pages of English Translation and 6 pages of Original Document).
International Search Report and Written Opinion received for PCT Patent Application No. PCT/EP2020/067683, dated Sep. 10, 2020, 11 pages (2 pages of English Translation and 9 pages of Original Document).
Klaus-Dieter Henkel, "Chapter 3—Reactor Types and Their Industrial Applications", Ullmann's Encyclopedia of Industrial Chemistry, ed. Ley, et al., vol. 31, 2000, pp. 293-327.
Nuzzo, et al., "Synthesis of functional chelating diphosphines containing the bis[2-(diphenylphosphino)ethyl]amino moiety and the use of these materials in the preparation of water-soluble diphosphine complexes of transition metals", The Journal of Organic Chemistry, vol. 46, Issue 14, 1981, pp. 2861-2867.
Saudan, et al., "Dihydrogen Reduction of Carboxylic Esters to Alcohols under the Catalysis of Homogeneous Ruthenium Complexes: High Efficiency and Unprecedented Chemoselectivity", Angewandte Chemie International Edition, vol. 46, Issue 39, 2007, pp. 7473-7476.

(Continued)

*Primary Examiner* — Rosalynd A Keys
(74) *Attorney, Agent, or Firm* — Faegre Drinker Biddle & Reath LLP

(57) ABSTRACT

Method for hydrogenating an ester with molecular hydrogen to the corresponding alcohols in the presence of a ruthenium complex (I), wherein said complex comprises a tridentate ligand L of the general formula (II)

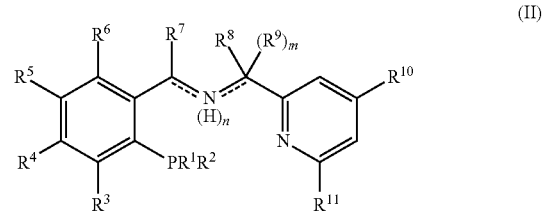

n and m are each independently 0 or 1, and the solid-dashed double lines represent a single or double bond, with the proviso that in the case of n=1 both solid-dashed double lines represent a single bond and m is 1, and in the case of n=0 one solid-dashed double line represents a single bond and the other solid-dashed double line represents a double bond, wherein in the case of a double bond on the side facing the phenyl ring m=1, in the case of a double bond on the side facing the pyridyl ring m=0, or both solid-dashed double lines represent a single bond and m is 1.

10 Claims, No Drawings

(56) References Cited

OTHER PUBLICATIONS

Wang, et al., "New Ruthenium Complexes Based on Tetradentate Bipyridine Ligands for Catalytic Hydrogenation of Esters", Chemistry an Asian Journal, vol. 11, Issue 15, 2016, pp. 2103-2106.
Zhang, et al., "Efficient Homogeneous Catalytic Hydrogenation of Esters to Alcohols", Angewandte Chemie International Edition, vol. 45, Issue 7, 2006, pp. 1113-1115.
Zotto et al., "[RuCl 2 (PPh 3 )(PNN')] Complexes as Efficient Catalysts in Transfer Hydrogenation of Ketones", Organometallics, vol. 26. No 23, Nov. 1, 2007, pp. 5636-5642.

* cited by examiner

HYDROGENATION OF ESTERS TO ALCOHOLS IN THE PRESENCE OF A RU-PNN COMPLEX

CROSS-REFERENCE TO RELATED APPLICATIONS

This application is a national stage application (under 35 U.S.C. § 371) of PCT/EP2020/067683, filed Jun. 24, 2020, which claims benefit of European Application Nos. 19184178.2, filed Jul. 3, 2019, and 20171976.2, filed Apr. 29, 2020, all of which are incorporated herein by reference in their entirety.

The present invention relates to a method for hydrogenating an ester with molecular hydrogen to give the corresponding alcohols in the presence of a ruthenium complex having a tridentate PNN ligand.

Alcohols are not only important solvents, they are also important intermediates and synthetic units, for example for the production of pharmaceuticals, plant protection agents or fragrances. Depending on the type of alcohol desired and the availability of the corresponding starting material, direct hydrogenation of the corresponding ester with hydrogen or reduction with reducing agents are often the methods of choice.

The synthesis of alcohols from esters is usually effected through the use of metal hydrides such as $LiAlH_4$ or $NaBH_4$, by heterogeneous catalytic hydrogenation with hydrogen, or by homogeneous catalytic hydrogenation with hydrogen. Homogeneous catalytic hydrogenations with hydrogen often allow less drastic reaction conditions with better selectivity at the same time. In particular, the use of ruthenium complexes having multidentate phosphorus, sulfur and nitrogen-containing ligands has proven successful in this respect according to the prior art.

For example, U.S. Pat. No. 8,013,193 describes the use of Ru complexes having triphos ligands such as 1,1,1-tris(diphenylphosphinomethyl)ethane in the hydrogenation of lactones and esters. The complexes mentioned, however, show a rather low reaction rate. An acceptable reaction rate can only be achieved by using very specific activating solvents (2,2,2-trifluoroethanol). However, the solvents added must then be separated off again from the product.

Another disadvantage of the triphos ligands is the high phosphorus/ruthenium molar ratio of three. Phosphine ligands are complex to manufacture. In addition, the three phosphino groups result in a relatively high molar mass of the complex ligand and of the Ru complex to be used. High molar masses are fundamentally disadvantageous in terms of general handling. In addition, the subsequent disposal of the used Ru complex is more costly, as more mass has to be disposed of and, moreover, phosphorus-containing components require special disposal.

A series of different publications describe Ru complexes having tetradentate PNNP ligands for the hydrogenation of esters to alcohols. For instance, Saudan et al. in Angewandte Chemie International Edition 2007, Vol. 46, pages 7473-7476, U.S. Pat. Nos. 7,989,665, 8,124,816, 8,524,953 and 9,193,651, inter alia, disclose the use of ligands of the type

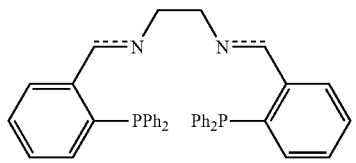

where the dashed line in each case represents an optional double bond. Further ligands in the sixfold coordinated Ru complex are, in particular, Cl, H, $BH_4$, CO, OH, alkoxy, carboxy and monophosphine. Based on a test series on Ru complexes having bidentate and tetradentate P- and N-containing ligands, Saudan et al. point out in the aforementioned article that two amino-phosphino bridged ligands are required in the Ru complex for the hydrogenation of esters to alcohols. These may be in the form of a PNNP ligand or two PN ligands in the Ru complex.

The disadvantage of using a Ru complex having one PNNP ligand or two PN ligands is the high phosphorus/ruthenium molar ratio of two. As already described above, phosphine ligands are complex to manufacture. In addition, they lead to a relatively high molar mass of the Ru complex, which is disadvantageous due to its lower atom economy (more mass per catalyst complex) compared to smaller catalyst complexes having the same catalytic activity.

The disadvantages of a high phosphorus content are also shown by the tridentate PNP ligand, described in U.S. Pat. No. 8,471,048, of the general structure

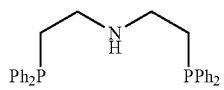

which has also previously been described for the Ru-catalyzed hydrogenation of esters and of ketones and lactones to alcohols.

The disadvantage of this ligand is the complex synthesis via bis(2-chloroethyl)ammonium chloride and reaction thereof with diphenylphosphine and potassium tert-butoxide and subsequent work-up with HCl (see Whitesides et al. in J. Org. Chem. 1981, Vol. 46, pages 2861-2867).

Milstein et al. describe in Angewandte Chemie International Edition 2006, Vol. 45, pages 1113-1115 the use of Ru complexes having a so-called pincer ligand of the PNN type for the hydrogenation of esters to alcohols. The tridentate pincer ligand described has a pyridyl group as backbone and a phosphino and amino group, each having low molecular weight alkyl groups, as donor groups. Mentioned by name here is the use of (2-(di-tert-butylphosphinomethyl)-6-(diethylaminomethyl) pyridine

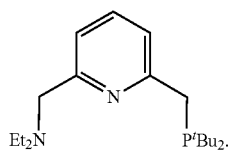

Similar pincer ligands of the PNN type for the hydrogenation of esters to alcohols are also described in U.S. Pat. No. 8,178,723 and US 2017/0,283,447.

The disadvantage of using the pincer ligands of the PNN type mentioned is their complex, multi-stage synthesis using sophisticated reagents starting from 2,6-dimethylpyridine, reaction thereof with N-bromosuccinimide and diethylamine to give 2-diethylaminomethyl-6-methylpyridine, and subsequent activation of the methyl group thereof by reaction with butyllithium and the final addition of the $P^tBu_2$ group by reaction with ditert-butylphosphine.

US 2014/0,328,748 teaches the Ru-catalyzed hydrogenation of esters and lactones to alcohols, catalyzed by a Ru complex having a PNN ligand, which is characterized by a nitrogen-containing heterocycle, an aliphatic bridge to an amine nitrogen and from this by a further aliphatic bridge having a length of at least two carbons to a phosphino group. Cited as typical representatives of this category are PNN ligands of the structure

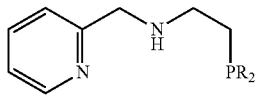

where R is an alkyl radical such as isopropyl or tert-butyl or a phenyl radical.

This ligand is also only accessible by a complex synthesis due to the —NH—$CH_2CH_2$—$PR_2$ unit. For example, the synthetic unit $H_2N$—$CH_2CH_2$—$PR_2$ is usually produced by reacting $HPR_2$ with 2-chloroethylamine, which is difficult to obtain, and HCl. Furthermore, phosphines with the structural unit —$CH_2CH_2$—$PR_2$ (where R=iPr) are relatively sensitive to oxidation, which has a negative effect due to the low storage stability of the ligand or increased expense in handling due to the use of a protective gas atmosphere.

In Chemistry An Asian Journal 2016, Vol. 11, pages 2103-2106, Zhang et al. disclose the use of a Ru complex having a tetradentate bipyridine ligand as catalyst for the hydrogenation of esters to alcohols. Specifically, it deals with the two PNNN ligands

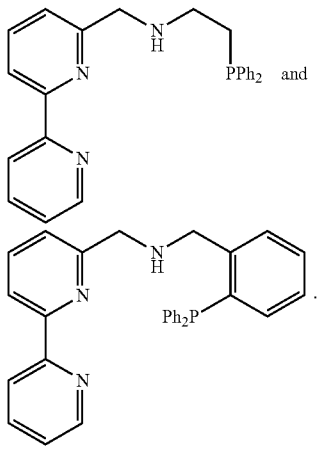

The authors teach that the bipyridine fragment is essential for high catalyst activity and relevant for achieving high acidity of the NH group.

These ligands also have significant disadvantages. For instance, their synthesis is complex from common synthetic units due to the bipyridine fragment. Starting from 2-bromopyridine and 2-(diphenylphosphaneyl)ethylamine or (2-(diphenylphosphaneyl)phenyl)methylamine, each requires a four-stage synthesis using n-butyllithium. The ligand shown above with the —$CH_2C_6H_4$—$PPh_2$ unit also has a relatively high molar mass. The negative effects of a higher molar mass are already mentioned above. Furthermore, the catalytic investigations in the literature reference cited show that the ligand with the —$CH_2C_6H_4$—$PPh_2$ unit enables yields of >60% only in toluene as solvent and also in the presence of sodium alkoxides as base.

In Organometallics 2007, Vol. 26, pages 5636-5642, Rigo et al. teach the use of tridentate PNN ligands of the structures

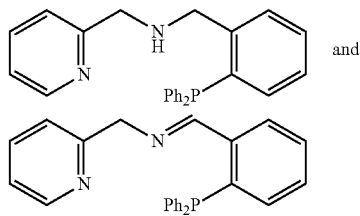

after reaction thereof with $RuCl_2(PPh_3)_3$ to the corresponding Ru complex, in the transfer hydrogenation of ketones with 2-propanol to the corresponding secondary alcohol and acetone. In transfer hydrogenation, therefore, the reducing reagent used is not hydrogen but a reducing compound such as a secondary alcohol or HCOOH/amine. However, it is known that catalysts which are well suited for transfer hydrogenation of ketones to alcohols are usually not sufficiently active in the hydrogenation of esters to alcohols. Transfer hydrogenation catalysts for ketones differ structurally and in terms of their reactivity from hydrogenation catalysts for esters.

For instance, Noyori et al. in Journal of the American Chemical Society 1996, Vol. 118, pages 2521-2522 show that a Ru complex that is highly suitable for the transfer hydrogenation of ketones to alcohols, specifically (R)—RuCl [(1S,2S)-p-TsNCH($C_6H_5$)CH—($C_6H_5$)$NH_2$](η-mesitylene), easily achieves yields of 99% in the transfer hydrogenation of ketones, but only allows a yield of 5% in hydrogenation with hydrogen. In addition, Noyori et al. also show, that in the case of substrates which also have an ester function in addition to a keto function, only the keto function, but not the ester function, is reduced to the corresponding alcohol in the transfer hydrogenation.

WO 2017/134,618 discloses the use of monocarbonyl complexes of ruthenium and osmium, which also comprise a nitrogen- and phosphorus-containing ligand, in the transfer hydrogenation of ketones and aldehydes and the hydrogenation of ketones and aldehydes with hydrogen to give the corresponding alcohols. Among the large number of nitrogen- and phosphorus-containing ligands mentioned, also disclosed, inter alia, is a tridentate PNN ligand of the structure

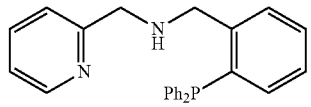

WO 2017/134,618 confirms by many examples that Ru complex catalysts which achieve high yields in the transfer hydrogenation of ketones have significantly poorer conversions in the hydrogenation with hydrogen. For instance, the Ru complex catalysts with the numbers 16, 20 and 22 in the transfer hydrogenation of acetophenone with 2-propanol to give 1-phenylethanol each show 100% conversion, whereas the same Ru complex catalysts in the hydrogenation of acetophenone with hydrogen only enable conversions of 25 to 63%. The Ru complex catalyst with the aforementioned PNN ligand ([Ru(OAc)$_2$(CO)(PNN)] with the number 39) achieved only 96% conversion in the transfer hydrogenation of acetophenone with 2-propanol to 1-phenylethanol and was not tested in the hydrogenation of acetophenone with hydrogen.

In summary, it can be stated that the ligands described in the prior art for the homogeneously catalyzed hydrogenation of esters to alcohols have relatively high molar masses, and/or are relatively complex and laborious to produce, and/or have only a rather low chemical stability. In addition, it is generally known that ligands which result in very good results in the transfer hydrogenation of ketones to alcohols are usually less suitable as a reducing agent in hydrogenation with hydrogen and, in particular, are unsuitable in most cases in the hydrogenation of esters.

The object of the present invention was to find a method for homogeneously catalyzed hydrogenation of esters to the corresponding alcohols which does not have the stated disadvantages of the prior art or only to a minor extent, is easy to carry out with regard to the apparatus required and reaction conditions and which enables the highest possible space-time yield.

In particular, the catalytically active complex should be directly preparable from readily available feedstocks, have high activity in the hydrogenation of esters to alcohols and ultimately be disposable without undue expense. In this context, the complex-forming ligand is of particular importance. In order to manage with as little catalyst mass as possible, a preferred ligand must have the lowest possible molar mass with comparable catalyst activity and also comparable expense in terms of preparation. In addition, high chemical stability of the ligand is desirable so that it is storage-stable prior to use without particularly complex measures and also remains stable during use.

In addition, the catalytically active complex can be used for the hydrogenation of a large number of esters regardless of their molar mass and further structure.

Surprisingly, a method for the hydrogenation of an ester with molecular hydrogen to give the corresponding alcohols at a temperature of 50 to 200° C. and a pressure of 0.1 to 20 MPa abs in the presence of a five-fold or six-fold coordinated ruthenium complex (I) has been found, wherein the ruthenium complex can also be bridged to form a dimer, in which the ruthenium complex comprises a tridentate ligand L of the general formula (II)

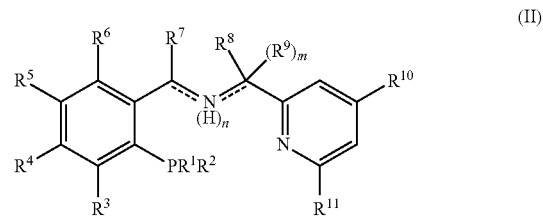

where

R$^1$, R$^2$ are each independently an aliphatic hydrocarbon radical having 1 to 8 carbon atoms, an aromatic hydrocarbon radical having 6 or 10 carbon atoms or an araliphatic hydrocarbon radical having 7 to 12 carbon atoms, where the hydrocarbon radicals specified are unsubstituted or substituted by 1 to 3 methoxy, thiomethoxy or dimethylamino groups, and the two radicals R$^1$ and R$^2$ may be bonded to each other to form a 5- to 10-membered ring including the phosphorus atom, R$^3$, R$^4$, R$^5$, R$^6$, R$^{10}$, R$^{11}$ are each independently hydrogen, linear C$_1$ to C$_4$-alkyl, branched C$_3$ to C$_4$-alkyl, methoxy, hydroxyl, trifluoromethyl, nitrile or dialkylamino each independently having 1 to 4 carbon atoms per alkyl group, R$^7$, R$^8$, R$^9$ are each independently hydrogen, linear C$_1$ to C$_4$-alkyl or branched C$_3$ to C$_4$-alkyl, n, m are each independently 0 or 1, and the solid-dashed double lines are a single or double bond, with the proviso that in the case of n=1, both solid-dashed double lines represent a single bond and m is 1, and in the case of n=0, one solid-dashed double line represents a single bond and the other solid-dashed double line represents a double bond, wherein in the case of a double bond on the side facing the phenyl ring, m=1, in the case of a double bond on the side facing the pyridyl ring m=0, or both solid-dashed double lines represent a single bond and m is 1.

The core of the method according to the invention is the use of a five-fold or six-fold coordinated ruthenium complex (I), which comprises a tridentate ligand L of the general formula (II), in the hydrogenation of esters with molecular hydrogen to give the corresponding alcohols.

The tridentate ligand L is a so-called PNN ligand of the general formula (II)

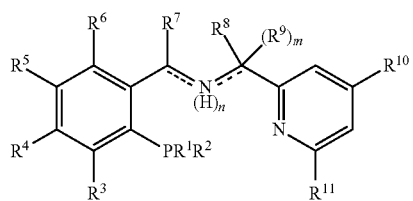

in which

R$^1$, R$^2$ are each independently an aliphatic hydrocarbon radical having 1 to 8 carbon atoms, an aromatic hydrocarbon radical having 6 or 10 carbon atoms or an araliphatic hydrocarbon radical having 7 to 12 carbon atoms, where the hydrocarbon radicals specified are unsubstituted or substituted by 1 to 3 methoxy, thiomethoxy or dimethylamino groups, and the two radicals R$^1$ and R$^2$ may be bonded to each other to form a 5- to 10-membered ring including the phosphorus atom, R$^3$, R$^4$, R$^5$, R$^6$, R$^{10}$, R$^{11}$ are each independently hydrogen, linear C$_1$ to C$_4$-alkyl, branched C$_3$ to C$_4$-alkyl, methoxy, hydroxyl, trifluoromethyl, nitrile or dialkylamino each independently having 1 to 4 carbon atoms per alkyl group, R$^7$, R$^8$, R$^9$ are each independently hydrogen, linear C$_1$ to C$_4$-alkyl or branched C$_3$ to C$_4$-alkyl, n, m are each independently 0 or 1, and the solid-dashed double lines are a single or double bond, with the proviso that in the case of n=1, both solid-dashed double lines represent a single bond and m is 1, and in the case of n=0, one solid-dashed double line represents a single bond and the other solid-dashed double line represents a double bond, wherein in the case of a double bond on the side facing the phenyl ring, m=1, in the case of a double bond on the side facing the pyridyl ring m=0, or both solid-dashed double lines represent a single bond and m=1.

Tridentate means that ligand L (II) occupies three coordination sites in the ruthenium complex (I). The three ligand donor atoms are the P and the two N atoms, from which the name PNN ligand is derived.

With respect to the environment of the central donor atom, the ligand can in principle have four different substructures, which are explained in more detail below.

(1) In the case of n=1, both solid-dashed double lines represent a single bond and m is 1. This results in the general formula (IIa). Ligand (IIa) is neutral, so it has a charge of "0".

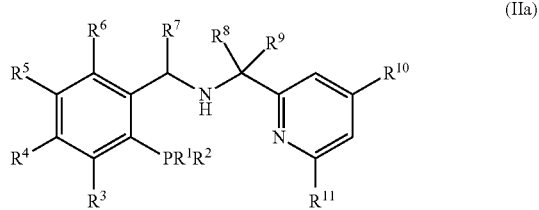

(IIa)

In the case of n=0, there are a total of three different substructures.

(2) If n=0 and the solid-dashed double line facing the phenyl ring is a double bond and the solid-dashed double line facing the pyridyl ring is a single bond, then m is equal to 1. This results in the general formula (IIb). Ligand (IIb) is neutral, so it has a charge of "0".

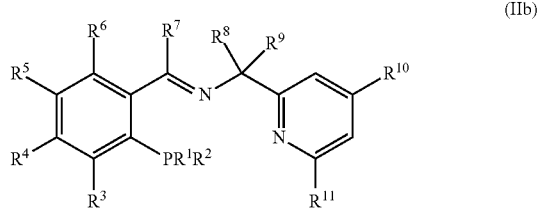

(IIb)

(3) If n=0 and the solid-dashed double line facing the pyridyl ring is a double bond and the solid-dashed double line facing the phenyl ring is a single bond, then m is equal to 0. This results in the general formula (IIc). Ligand (IIc) is neutral, so it has a charge of "0".

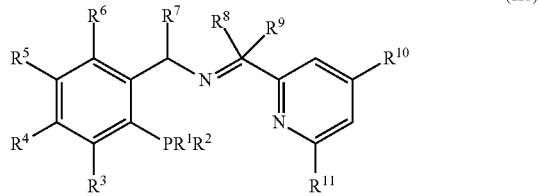

(IIc)

(4) In the fourth variant, n=0 also, but both solid-dashed double lines are single bonds and m is 1. The N atom therefore has a negative charge. This results in the general formula (IId). The ligand (IId) thus has a charge of "−1".

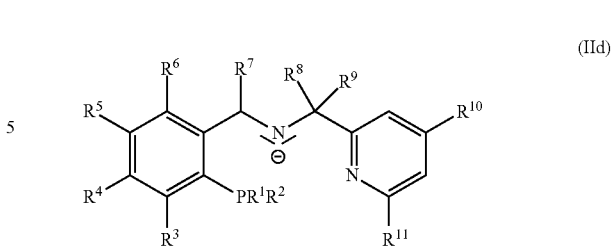

(IId)

The radicals $R^1$ and $R^2$ of the ligand (II) may vary to a wide extent and are each independently an aliphatic hydrocarbon radical having 1 to 8 carbon atoms, an aromatic hydrocarbon radical having 6 or 10 carbon atoms or an araliphatic hydrocarbon radical having 7 to 12 carbon atoms, where the hydrocarbon radicals specified may be unsubstituted or substituted by 1 to 3 methoxy, thiomethoxy or dimethylamino groups, and the two radicals $R^1$ and $R^2$ may also be bonded to each other to form a 5- to 10-membered ring including the phosphorus atom.

In the case of one aliphatic hydrocarbon radical, this may be unbranched or branched or linear or cyclic. The aliphatic hydrocarbon radical preferably has 1 to 6 carbon atoms, particularly preferably 1 to 4 carbon atoms and especially preferably 1 to 2 carbon atoms. Specific examples that may be mentioned are methyl, ethyl, isopropyl, n-propyl, n-butyl, isobutyl, tert-butyl (also referred to as tBu) and cyclohexyl (also referred to as Cy).

In the case of one aromatic hydrocarbon radical, this is phenyl (also referred to as Ph), 1-naphthyl or 2-naphthyl.

Araliphatic hydrocarbon radicals comprise aromatic and aliphatic elements, regardless of whether these are bonded to the phosphorus atom in the ligand L via an aliphatic or an aromatic group. The araliphatic hydrocarbon radicals preferably have 7 to 10 carbon atoms and particularly preferably 7 to 9 carbon atoms. Specific examples that may be mentioned are o-tolyl, m-tolyl, p-tolyl and benzyl.

In the case of one ring including the phosphorus atom, it is preferably a ring having 5 to 6 atoms, including the phosphorus atom. Examples which may be mentioned are butane-1,4-diyl, pentane-1,5-diyl and 2,4-dimethylpentane-1,5-diyl.

The aliphatic, aromatic and araliphatic hydrocarbon radicals mentioned, which may also be bonded to one another to form a ring including the phosphorus atom, may be unsubstituted or substituted by 1 to 3 methoxy, thiomethoxy or dimethylamino groups. The number of carbon atoms of the individual hydrocarbon radicals specified above is to be understood as including the carbon atoms of the methoxy, thiomethoxy or dimethylamino groups. Specific examples that may be mentioned are 3,5-dimethylphenyl, 3,5-dimethyl-4-methoxyphenyl, 3,5-dimethyl-4-thiomethoxyphenyl and 3,5-dimethyl-4-(dimethylamino)phenyl.

The radicals $R^1$ and $R^2$ are particularly preferably phenyl, p-tolyl, o-tolyl, 4-methoxyphenyl, 2-methoxyphenyl, cyclohexyl, isobutyl, tert-butyl, 3,5-dimethyl-4-methoxyphenyl, 3,5-tert-butyl-4-methoxyphenyl and 3,5-dimethylphenyl and especially preferably phenyl, p-tolyl, 3,5-dimethyl-4-methoxyphenyl, isobutyl and cyclohexyl, where preferably both radicals are the same.

The radicals $R^3$, $R^4$, $R^5$, $R^6$, $R^{10}$ and $R^{11}$ are each independently hydrogen, linear $C_1$ to $C_4$-alkyl, branched $C_3$ to $C_4$-alkyl, methoxy, hydroxyl, trifluoromethyl, nitrile or dialkylamino each independently having 1 to 4 carbon atoms per alkyl group. To be mentioned as linear $C_1$ to $C_4$-alkyl are methyl, ethyl, n-propyl and n-butyl and as branched $C_3$ to $C_4$-alkyl are isopropyl, sec-butyl and tert-butyl. As dialkylamino, there should be mentioned in particular amino radicals having identical alkyl groups, in particular dimethylamino, diethylamino, di-n-propylamino and di-n-butylamino.

The radicals $R^3$ and $R^4$ are preferably each independently hydrogen or methyl and particularly preferably hydrogen.

The radical $R^5$ is preferably hydrogen, methyl, isopropyl, sec-butyl, tert-butyl, methoxy, hydroxyl or dialkylamino, particularly preferably hydrogen, methyl or hydroxyl and especially preferably hydrogen.

The radical $R^6$ is preferably hydrogen.

The radical $R^{10}$ is preferably hydrogen, methyl, isopropyl, sec-butyl, tert-butyl or methoxy, particularly preferably hydrogen, methyl or tert-butyl and especially preferably hydrogen.

The radical $R^{11}$ is preferably hydrogen, methyl, ethyl, methoxy, ethoxy or isopropyloxy and particularly preferably hydrogen, methyl or methoxy.

Especially preferred are ligands (II) in which
$R^3$, $R^4$, $R^5$, $R^6$, $R^{10}$ and $R^{11}$ are hydrogen,
$R^3$, $R^4$, $R^5$, $R^6$ and $R^{10}$ are hydrogen and $R^{11}$ is methyl,
$R^3$, $R^4$, $R^5$, $R^6$ and $R^{10}$ are hydrogen and $R^{11}$ is methoxy,
$R^3$, $R^4$, $R^6$, $R^{10}$ and $R^{11}$ are hydrogen and $R^5$ is methyl,
$R^3$, $R^4$, $R^6$, $R^{10}$ and $R^{11}$ are hydrogen and $R^5$ is tert-butyl,
$R^3$, $R^4$, $R^5$, $R^6$ and $R^{11}$ are hydrogen and $R^{10}$ is methyl,
$R^3$, $R^4$, $R^5$, $R^6$ and $R^{11}$ are hydrogen and $R^{10}$ is tert-butyl, and
$R^3$, $R^4$, $R^5$ and $R^6$ are hydrogen and $R^{10}$ and $R^{11}$ are methyl.

The radicals $R^7$, $R^8$ and $R^9$ are each independently hydrogen, linear $C_1$ to $C_4$-alkyl or branched $C_3$ to $C_4$-alkyl. To be mentioned as linear $C_1$ to $C_4$-alkyl are methyl, ethyl, n-propyl and n-butyl and as branched $C_3$ to $C_4$-alkyl are isopropyl, sec-butyl and tert-butyl.

The radicals $R^7$, $R^8$ and $R^9$ are preferably each independently hydrogen, methyl, ethyl or n-propyl, particularly preferably hydrogen or methyl and especially preferably hydrogen.

Especially preferred are ligands (II) in which
$R^7$, $R^8$ and $R^9$ are hydrogen,
$R^7$ and $R^9$ are hydrogen and $R^8$ is methyl,
$R^7$ is hydrogen and $R^8$ and $R^9$ are methyl,
$R^7$ is methyl and $R^8$ and $R^9$ are hydrogen, and
$R^7$ and $R^8$ are methyl and $R^9$ is hydrogen.

Particularly advantageous in the method according to the invention is the use of the ligands (II), in which
(i) n and m are in each case 1 and the two solid-dashed double lines represent a single bond (structure (IIa)), or
(ii) n is 0 and m is 1 and the solid-dashed double line facing the phenyl ring represents a double bond and the solid-dashed double line facing the pyridyl ring represents a single bond (structure (IIb),
and
both radicals $R^1$ and $R^2$ are phenyl, p-tolyl, 3,5-dimethyl-4-methoxyphenyl, isobutyl or cyclohexyl,
the radicals $R^3$, $R^4$ and $R^6$ are hydrogen,
the radicals $R^5$ and $R^{10}$ are hydrogen, methyl or tert-butyl,
the radical $R^{11}$ is hydrogen, methyl or methoxy, and
the radicals $R^7$, $R^8$ and $R^9$ are hydrogen or methyl.

Ligand (II) can be obtained in a simple manner by condensation of a corresponding amine with a corresponding aldehyde or ketone (ligand (IIb) and (IIc)) and a possible subsequent reduction (ligand (IIa)) and a possible subsequent deprotonation under basic conditions (ligand (IId)).

There are in principle two different possibilities for the condensation. Firstly, it is possible to use 2-picolylamine or a corresponding derivative thereof as the amine component, and an appropriately substituted phosphanylbenzaldehyde or a corresponding ketone as the aldehyde or ketone component.

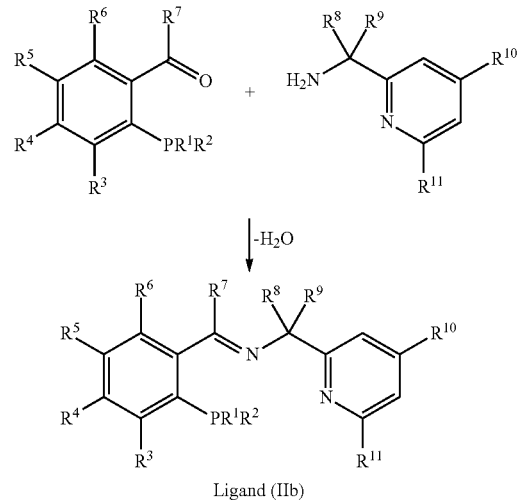

Ligand (IIb)

Secondly, it is, however, also possible to use an appropriately substituted phosphanylphenylmethanamine as the amine component and picolinaldehyde or a corresponding derivative thereof as the aldehyde or ketone component.

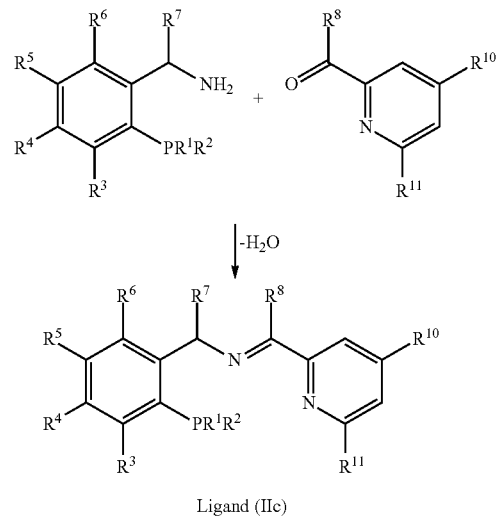

Ligand (IIc)

The corresponding starting compounds (amines, ketones or aldehydes) are generally commercially available or can be synthesized using generally known methods. The synthesis of the ligands (IIb) and (IIc) is usually carried out under a protective gas atmosphere. The two components are typically reacted with each other in a solvent at a temperature of 50 to 200° C. Suitable solvents include, for example, aliphatic alcohols such as methanol, ethanol or isopropanol and aromatic hydrocarbons such as toluene or xylenes. The two starting compounds may be used in stoichiometric amounts. However, it is also possible to use one of the two components in excess, for example in order to increase the conversion of the other component. This is particularly useful if the other component is difficult to access. If an excess is used, the molar ratio of the two starting compounds is generally in the range from >1 to ≤2. The reaction time typically ranges from a few minutes to several hours. A typical reaction time that may be mentioned is 10 minutes to 5 hours and preferably 30 minutes to 3 hours. The reaction mixture may be worked up and the ligand isolated by customary methods. However, the solvent and water added are advantageously removed under reduced pressure.

The ligands (IIb) and (IIc) may now be used to prepare the ruthenium complex (I).

A particularly elegant and therefore also preferred variant is the synthesis of the ligands (IIb) and (IIc) together with the preparation of the ruthenium complex (I) in a one-pot reaction. For this purpose, the starting compounds (amines and ketone or aldehyde) are first reacted with each other as described above, but then not worked up and isolated, but instead the corresponding ruthenium precursor and, optionally, a base for forming the catalytically active ruthenium complex (I) are added to the reaction mixture obtained. By adjusting the hydrogenation conditions and adding the ester to be hydrogenated, it is thus also very easy to prepare the ligand (II) in a one-pot reaction, then directly to prepare the ruthenium complex (I) therefrom and then to carry out the hydrogenation of the ester directly.

By reducing ligand (IIb) or (IIc) with reducing agents such as sodium borohydride or lithium aluminum hydride or catalytically with hydrogen, ligand (IIa) may be obtained in a simple manner from ligands (IIb) and (IIc). The reaction can be carried out with the common knowledge of those skilled in the art.

In a particularly advantageous synthesis, the condensation described above and the reduction to the ligand (IIa) are carried out directly one after the other in a one-pot reaction without isolating the ligands (IIb) and (IIc) beforehand. To this end, after the condensation has ended, the reducing agent is added directly to the reaction mixture and allowed to react with each other for a further period of time. A few minutes to several hours are usually sufficient here also. A typical reaction time that may be mentioned is 10 minutes to 5 hours and preferably 30 minutes to 3 hours. The reaction mixture can then be worked up and the ligand isolated by customary methods. Explicit reference is made to the information given on the work-up and isolation of the ligands (IIb) and (IIc).

Ligand (IIa) is formed from ligands (IIb) and (IIc), also bonded in the ruthenium complex (I) under the reaction conditions by hydrogenation with the hydrogen supplied.

The anionic ligand (IId) is formed from ligand (IIa), as a result of the elimination of the hydrogen atom on the nitrogen as a proton, by reaction with a strong base. Suitable strong bases are, for example, NaOMe or KOMe. Usually, this reaction is not carried out specifically with the free ligand (IIa). Rather, the ligand (IId) can form in the ruthenium complex (I) under hydrogenation conditions in the presence of a strong base.

The ruthenium complex (I) to be used in the method according to the invention is five-fold or six-fold coordinated. Three of these coordination positions are already occupied by the tridentate ligand (II). The ruthenium complex (I) can be mononuclear or binuclear, i.e. also bridged as a dimer. If the ruthenium complex (I) is bridged to form a dimer, this has two ruthenium atoms in the complex.

In the method according to the invention, the oxidation state of the ruthenium in the ruthenium complex (I) is not restricted. Usually, however, this is 0 (zero), +2 or +3 and preferably +2 or +3.

The ruthenium complex (I) preferably used in the method according to the invention comprises ruthenium in the oxidation state +2 or +3 and has the general formula (IA)

$$[Ru(L)X_aY_b]_pZ_{(p\cdot c)} \quad (IA)$$

where
X is in each case independently a neutral monodentate ligand, where two ligands X may also be bonded to form a neutral bidentate ligand,
Y is in each case independently an anionic monodentate ligand having a charge of "−1",
where Y and X together may also be an anionic bidentate ligand having a charge of "−1",
Z is in each case independently a non-coordinating anion having a charge of "−1", where two ligands Z may also be bonded to form a non-coordinating anion having a charge of "−2",
a, b and c are each independently 0, 1, 2 or 3, and
p is 1 or 2,
with the provisos that
a+b+c equals 1, 2, 3, 4, 5 or 6, and
b and c are determined such that the ruthenium complex (IA) has a total charge of "0".

In the ruthenium complex (IA), the indices a, b and c each specify the number of the respective ligands X, Y and of the non-coordinating counterion Z, based on one ruthenium atom. Since ligand (II) is tridentate and the ruthenium complex (IA) has a maximum six-fold coordination, the maximum value of the indices is 3 in each case.

The index p indicates whether the ruthenium complex (IA) is mononuclear (p=1) or binuclear (p=2).

By observing further boundary conditions, it follows that the sum of a, b and c can only assume the values 1, 2, 3, 4, 5 and 6. Since the ruthenium complex (IA) is defined as neutral overall, no arbitrary combinations for a, b and c are possible.

For the sake of completeness, it should be explicitly pointed out that the index "(p·c)" in the general formula (IA) is the product of "p times c".

The preferred ruthenium complex (IA) in the process according to the invention is a ruthenium complex in which
X is in each case independently a neutral ligand selected from the group comprising CO, $NH_3$, $NR_3$, $R_2NSO_2R$, $PR_3$, $AsR_3$, $SbR_3$, $P(OR)_3$, $SR_2$, RCN, RNC, $N_2$, NO, $PF_3$, pyridine, thiophene, tetrahydrothiophene and N-heterocyclic carbene of the general formulae

(Xa)

and

(Xb)

or two ligands X together are 1,5-cyclooctadiene,
Y is in each case independently an anionic ligand selected from the group comprising $H^-$, $F^-$, $Cl^-$, $Br^-$, $I^-$, $OH^-$, $C_1$ to $C_6$-alkoxy, $C_1$ to $C_6$-carboxy, methylallyl, acetylacetonato, $RSO_3^-$, $CF_3SO_3^-$, $CN^-$ and $BH_4^-$, or one Y together with one X is $C_1$ to $C_6$-carboxy or acetylacetonato; and Z is in each case independently a non-coordinating anion selected from the group comprising $H^-$, $F^-$, $C^-$, $Br^-$, $I^-$, $OH^-$, $BF_4^-$, $PF_6^-$, $NO_3^-$, $RCOO^-$, $CF_3COO^-$, $CH_3SO_3^-$, $CF_3SO_3^-$, $BH_4^-$, $NH_2^-$, $RO^-$, $CN^-$, $R_2N-$, $SCN^-$, $OCN^-$, $RS^-$, $R-CONH^-$, $(R-CO)_2N^-$, $HCO_3^-$, $HSO_4^-$, $H_2PO_4^-$, acetylacetonate, pentafluorobenzoate, bis(trimethylsilyl)amide and tetrakis[3,5-bis(trifluoromethyl)phenyl]borate or two ligands Z together are $CO_3^{2-}$, $SO_4^{2-}$, $HPO_4^{2-}$, $S^{2-}$, where the radicals R in the definitions of X, Y and Z are each independently $C_1$ to $C_{10}$-alkyl, $CF_3$, $C_2F_5$, $C_3$ to $C_{10}$-cycloalkyl, $C_3$ to $C_{10}$-heterocyclyl comprising at least one heteroatom selected from the group comprising N, O and S, $C_5$ to $C_{10}$-aryl or $C_5$ to $C_{10}$-hetaryl comprising at least one heteroatom selected from the group comprising N, O and S.

The radicals R are preferably each independently $C_1$ to $C_4$-alkyl, $C_5$ to $C_6$-cycloalkyl, o-tolyl, p-tolyl, xylyl or mesityl and particularly preferably methyl, xylyl or mesityl.

The neutral ligand X in the ruthenium complex (IA) is preferably CO, trimethylphosphine, triphenylphosphine, tricyclohexylphosphine, triphenyl phosphite or trimethyl phosphite, or two ligands X together are cycloocta-1,5-diene. The neutral ligand X is particularly preferably triphenylphosphine.

The anionic ligand Y in the ruthenium complex (IA) is preferably $H^-$, $Cl^-$, $OH^-$, $C_1$ to $C_4$-alkoxy, $C_1$ to $C_4$-carboxy, methylallyl, acetylacetonato or bis(trimethylsilyl)amide, or a ligand Y together with a ligand X is $C_1$ to $C_4$-carboxy or acetylacetonato. The anionic ligand Y is particularly preferably $H^-$, $Cl^-$, methoxy or acetate.

Anionic ligands with an anionic O— group and a neutral O═ group, which are linked to one another via an odd number of carbon atoms, such as carboxylates or acetylacetonate, can function both as monodentate and as bidentate ligands, such as the following examples with the acetate anion demonstrate.

If the complex with the ligands L, X and Y should have a positive charge, a corresponding number of non-coordinating anions Z is required to render the ruthenium complex (IA) neutral. In this case, preference is given to anions in which Z is $Cl^-$, $OH^-$, $C_1$ to $C_4$-alkoxide, $C_1$ to $C_4$-carboxylate, $BF_4^-$ or $PF_6^-$, or two Z together are $SO_4^{2-}$. The non-coordinating anion Z is particularly preferably $Cl^-$, methoxide, acetate, $BF_4^-$ or $PF_6^-$.

Particular preference is given to a method in which the ruthenium complex (IA) is selected from the group consisting of (a) ruthenium complex (IAa) of the general formula (IAa)

$$[Ru(L)X_{1+p}Y_{2-p}]Z_p \quad (IAa)$$

where p=0 or 1;

(b) ruthenium complex (IAb) of the general formula (IAb)

$$[Ru(L)X_pY_{2-p}]Z_p \quad (IAb)$$

where p=0 or 1;

(c) ruthenium complex (IAc) of the general formula (IAc)

$$[Ru(L)X_pY_{2-p}]_2Z_{2p} \quad (IAc)$$

where p=0 or 1;

(d) ruthenium complex (IAd) of the general formula (IAd)

$$[Ru(L)X_{p+1}Y_{1-p}]_2Z_{2p} \quad (IAd)$$

where p=0 or 1;

(e) ruthenium complex (IAe) of the general formula (IAe)

$$[Ru(L)X_pY_{3-p}]Z_p \quad (IAe)$$

where p=0 or 1;

(f) ruthenium complex (IAf) of the general formula (IAf)

$$[Ru(L)X_pY_{2-p}]Z_{1+p} \quad (IAf)$$

where p=0 or 1; and (g) ruthenium complex (IAg) of the general formula (IAg)

$$[Ru(L)X_{p-1}Y_{3-p}]_2Z_{2p} \quad (IAg)$$

where p=1;

(h) ruthenium complex (IAh) of the general formula (IAh)

$$[Ru(L)X_pY_{2-p}]_2Z_{2p} \quad (IAh)$$

where p=1.

Preferred examples of ruthenium complex (IAa) include [Ru(L)(PPh$_3$)Cl$_2$], [Ru(L)(PPh$_3$)Cl(OAc)], [Ru(L)(PPh$_3$)(H)(Cl)], [Ru(L)(PPh$_3$)(OAc)$_2$], [Ru(L)(PPh$_3$)acac(H)], [Ru(L)(PPh$_3$)(H)(OMe)], [Ru(L)(PPh$_3$)(H)$_2$], [Ru(L)(CO)(H)$_2$] [Ru(L)(PPh$_3$)(H)(OAlkyl)], [Ru(L)(PPh$_3$)(H)(OAc)], [Ru(L)(P(o-tolyl)$_3$)Cl$_2$], [Ru(L)(P(o-tolyl)$_3$)Cl(OAc)], [Ru(L)(P(o-tolyl)$_3$)(H)(Cl)], [Ru(L)(P(o-tolyl)$_3$)(OAc)$_2$], [Ru(L)(P(o-tolyl)$_3$)acac(H)], [Ru(L)(P(o-tolyl)$_3$)(H)(OMe)], [Ru(L)(P(o-tolyl)$_3$)(H)]OMe, [Ru(L)(P(o-tolyl)$_3$)(H)$_2$], [Ru(L)(P(o-tolyl)$_3$)(H)(OAlkyl)], [Ru(L)(P(o-tolyl)$_3$)(H)(OAc)], [Ru(L)(P(p-tolyl)$_3$)(Cl)$_2$], [Ru(L)(P(p-tolyl)$_3$)Cl(OAc)], [Ru(L)(P(p-tolyl)$_3$)(H)(Cl)], [Ru(L)(P(p-tolyl)$_3$)(OAc)$_2$], [Ru(L)(P(p-tolyl)$_3$)acac(H)], [Ru(L)(P(p-tolyl)$_3$)(H)(OMe)], [Ru(L)(P(p-tolyl)$_3$)H$_2$], [Ru(L)(P(p-tolyl)$_3$)(H)(OAlkyl)], [Ru(L)(P(p-tolyl)$_3$)(H)(OAc)], [Ru(L)(PCy$_3$)Cl$_2$], [Ru(L)(PCy$_3$)Cl(OAc)], [Ru(L)(PCy$_3$)(H)(Cl)], [Ru(L)(PCy$_3$)(OAc)$_2$], [Ru(L)(PCy$_3$)acac(H)], [Ru(L)(PCy$_3$)(H)(OMe)], [Ru(L)(PCy$_3$)H$_2$], [Ru(L)(PCy$_3$)(H)(OAlkyl)], [Ru(L)(PCy$_3$)(H)(OAc)], [Ru(L)(PtBu$_3$)Cl$_2$], [Ru(L)(PtBu$_3$)Cl(OAc)], [Ru(L)(PtBu$_3$)(H)(Cl)], [Ru(L)(PtBu$_3$)(OAc)$_2$], [Ru(L)(PtBu$_3$)acac(H)], [Ru(L)(PtBu$_3$)(H)(OMe)], [Ru(L)(PtBu$_3$)(H)$_2$], [Ru(L)(PtBu$_3$)(H)(OAlkyl)], [Ru(L)(PtBu$_3$)(H)(OAc)], [Ru(L)(P(OR)$_3$)Cl$_2$], [Ru(L)(CO)(H)(Cl)], [Ru(L)(CO)(H)(OAlk)], [Ru(L)(CO)(H)(OMe)], [Ru(L)(P(OR)$_3$)(H)$_2$], [Ru(L)(P(OR)$_3$)(H)(Cl)], [Ru(L)(P(OR)$_3$)(OAc)$_2$], where R is preferably methyl, ethyl, isopropyl, isobutyl, tert-butyl, phenyl, o-tolyl, p-tolyl, 2,4-dimethylphenyl or 2,4-di-tert-butylphenyl, [Ru(L)(P(OR)$_3$)acac], [Ru(L)(NHC)Cl$_2$], [Ru(L)(NHC)(OAc)$_2$], [Ru(L)(NHC)acac], [Ru(L)(PPh$_3$)(CO)(H)]Cl, [Ru(L)(PPh$_3$)(CO)(H)]OAc, [Ru(L)(P(o-tolyl)$_3$)(CO)(H)]Cl, [Ru(L)(P(o-tolyl)$_3$)(CO)(H)]OAc, [Ru(L)(P(p-tolyl)$_3$)(CO)(H)]Cl, [Ru(L)(P(p-tolyl)$_3$)(CO)(H)]OAc, [Ru(L)(PCy$_3$)(CO)(H)]Cl, [Ru(L)(PCy$_3$)(CO)(H)]OAc, [Ru(L)(PtBu$_3$)(CO)(H)]Cl, [Ru(L)(PtBu$_3$)(CO)(H)]OAc and [Ru(L)(CO)Cl$_2$], where L is in each case the neutral ligands (IIa), (IIb) or (IIc).

Preferred examples of ruthenium complex (IAb) include [Ru(L)H$_2$], [Ru(L)Cl$_2$], [Ru(L)OAc$_2$], [Ru(L)H(OMe)], [Ru(L)H(OAlk)], [Ru(L)(H)acac], [Ru(L)(H)(Cl)], [Ru(L)(H)OAc], [Ru(L)(PPh$_3$)OAc]Cl, [Ru(L)(PPh$_3$)(OMe)]Cl, [Ru(L)(PPh$_3$)(OMe)]OAc, [Ru(L)(PPh$_3$)(H)]OAc, [Ru(L)(PPh$_3$)(H)]OMe, [Ru(L)(CO)(H)]OMe, [Ru(L)(CO)(H)]OAc and [Ru(L)(PPh$_3$)Cl]OAc, where L is in each case the neutral ligands (IIa), (IIb) or (IIc).

Preferred examples of ruthenium complex (IAc) include [Ru(L)(PPh$_3$)Cl]$_2$Cl$_2$, [Ru(L)(Cl)$_2$]$_2$, [Ru(L)(OMe)$_2$]$_2$), where L is in each case the neutral ligands (IIa), (IIb) or (IIc), or also [Ru(L)(OMe)$_2$]$_2$, [Ru(L)(Cl)$_2$]$_2$, where L is in each case the anionic ligands (IId).

Preferred examples of ruthenium complex (IAd) include [Ru(L)(H)(PPh$_3$)]$_2$, [Ru(L)(H)(CO)]$_2$, [Ru(L)(Cl)(CO)]$_2$, [Ru(L)(Cl)(PPh$_3$)]$_2$, [Ru(L)(OMe)(CO)]$_2$, where L is in each case the anionic ligands (IId).

Preferred examples of ruthenium complex (IAe) include [Ru(L)(PPh$_3$)(Cl)$_2$]BF$_4$, [Ru(L)(PPh$_3$)(Cl)$_2$]PFe, [Ru(L)(PPh$_3$)(Cl)$_2$]OAc, [Ru(L)(PPh$_3$)(Cl)$_2$]acac, [Ru(L)(PPh$_3$)(H)(Cl)]BF$_4$, [Ru(L)(PPh$_3$)(H)(Cl)]PFe, [Ru(L)(PPh$_3$)(H)(Cl)]OAc, [Ru(L)(PPh$_3$)(H)(Cl)]OMe, [Ru(L)(CO)(H)(Cl)]BF$_4$, [Ru(L)(CO)(H)(Cl)]PFe, [Ru(L)(CO)(H)(Cl)]OAc, [Ru(L)(CO)(H)(Cl)]OMe, [Ru(L)(CO)(Cl)$_2$]BF$_4$, [Ru(L)(CO)(Cl)$_2$]PFe, [Ru(L)(CO)(Cl)$_2$]OAc, [Ru(L)(CO)(Cl)$_2$]OMe, [Ru(L)(OAc)$_2$]BF$_4$, [Ru(L)(OAc)$_2$]PFe and [Ru(L)(OAc)$_2$] OAc, where L is in each case the neutral ligands (IIa), (IIb) or (IIc).

Preferred examples of ruthenium complex (IAf) include [Ru(L)(PPh$_3$)(CF$_3$SO$_3$)](CF$_3$SO$_3$)$_2$, [Ru(L)(CO)(Cl)](OAc)$_2$, [Ru(L)(OAc)$_2$](OAc) and [Ru(L)(Cl)$_2$](Cl), where L is in each case the neutral ligands (IIa), (IIb) or (IIc).

Preferred examples of ruthenium complex (IAg) include [Ru(L)(Cl)$_2$]$_2$(BF$_4$)$_2$ and [Ru(L)(Cl)$_2$]$_2$(PFe)$_2$, where L is in each case the neutral ligands (IIa), (IIb) or (IIc).

Preferred examples of ruthenium complex (IAh) include [Ru(L)(PPh$_3$)(Cl)]$_2$(BF$_4$)$_2$, [Ru(L)(PPh$_3$)(Cl)]$_2$(PFe)$_2$, [Ru(L)(PPh$_3$)(Cl)]$_2$(OAc)$_2$, [Ru(L)(PPh$_3$)(Cl)]$_2$(acac)$_2$, [Ru(L)(CO)(Cl)]$_2$(BF$_4$)$_2$, [Ru(L)(CO)(Cl)]$_2$(PFe)$_2$, [Ru(L)(CO)(Cl)]$_2$(BF$_4$)$_2$, [Ru(L)(CO)(Cl)]$_2$(OAc)$_2$, [Ru(L)(CO)(Cl)]$_2$(acac)$_2$, where L is in each case the anionic ligands (IId).

Particularly preferred ruthenium complexes (IA) are the ruthenium complexes (IAa) and (IAc).

The method according to the invention is especially preferably carried out in the presence of ruthenium complexes (I) in which
- the ligand (II) is the ligands (IIa), (IIb) or (IIc) and in which
- the radicals $R^1$ and $R^2$ are in each case phenyl, p-tolyl, 3,5-dimethyl-4-methoxyphenyl, isobutyl or cyclohexyl,
- the radicals $R^5$ and $R^{10}$ are each independently hydrogen, methyl or tert-butyl,
- the radical $R^{11}$ is each independently hydrogen, methyl or methoxy,
- the radicals $R^7$, $R^8$ and $R^9$ are each independently hydrogen or methyl, and
- the ruthenium complexes (I) have the composition [Ru(L)(PPh$_3$)Cl$_2$], [Ru(L)(PPh$_3$)(H)(Cl)], [Ru(L)(PPh$_3$)(OAc)$_2$], [Ru(L)(PPh$_3$)H(acac)], [Ru(L)(PPh$_3$)(H)(OMe)], [Ru(L)(PPh$_3$)(H)]OMe, [Ru(L)(P(o-tolyl)$_3$)Cl$_2$], [Ru(L)(P(o-tolyl)$_3$)Cl(OAc)], [Ru(L)(P(o-tolyl)$_3$)(H)(Cl)], [Ru(L)(P(o-tolyl)$_3$)(OAc)$_2$], [Ru(L)(P(o-tolyl)$_3$)acac], [Ru(L)(P(o-tolyl)$_3$)(H)(OMe)], [Ru(L)(P(p-tolyl)$_3$)Cl$_2$], [Ru(L)(P(p-tolyl)$_3$)Cl(OAc)], [Ru(L)(P(p-tolyl)$_3$)(H)(Cl)], [Ru(L)(P(p-tolyl)$_3$)(OAc)$_2$], [Ru(L)(P(p-tolyl)$_3$)acac], [Ru(L)(P(p-tolyl)$_3$)(H)(OMe)], [Ru(L)(PCy$_3$)Cl$_2$], [Ru(L)(PCy$_3$)Cl(OAc)], [Ru(L)(PCy$_3$)(H)(Cl)], [Ru(L)(PCy$_3$)(OAc)$_2$], [Ru(L)(PCy$_3$)acac], [Ru(L)(PCy$_3$)(H)(OMe)], [Ru(L)(PtBu$_3$)Cl$_2$], [Ru(L)(PtBu$_3$)Cl(OAc)], [Ru(L)(PtBu$_3$)(H)(Cl)], [Ru(L)(PtBu$_3$)(OAc)$_2$], [Ru(L)(PtBu$_3$)acac], [Ru(L)(PtBu$_3$)(H)(OMe)], [Ru(L)(P(OR)$_3$)(OAc)$_2$], [Ru(L)H(OMe)], [Ru(L)H(OAlk)], [Ru(L)(P(OR)$_3$)acac], [Ru(L)(NHC)Cl$_2$], [Ru(L)(NHC)(OAc)$_2$], [Ru(L)(NHC)acac], [Ru(L)(PPh$_3$)OAc]Cl, [Ru(L)(PPh$_3$)(OMe)]Cl, [Ru(L)(PPh$_3$)(OMe)]OAc, [Ru(L)(PPh$_3$)Cl]OAc, [Ru(L)(PPh$_3$)(Cl)]$_2$OAc$_2$, [Ru(L)(PPh$_3$)(Cl)]$_2$Cl$_2$, [Ru(L)(Cl)$_2$]$_2$, [Ru(L)(OAc)$_2$]$_2$, [Ru(L)(OMe)$_2$]$_2$, [Ru(L)(H)(Cl)]$_2$ or [Ru(L)(H)(OAc)]$_2$.

The ruthenium complexes (I) to be used in the method according to the invention may be obtained in various ways. As ruthenium-containing starting material, one preferred possibility is to use a compound in which the ruthenium is already present in the form of a complex, hereinafter referred to as Ru precursor complex (IV), and to react this with the ligand L. Accordingly, a method is preferred in which the ruthenium complex (I) is obtained by reacting ligand (II) with a Ru precursor complex (IV).

In principle, a very wide variety of Ru complexes may be used as Ru precursor complex (IV). The Ru precursor complex (IV) is usually a five-fold or six-fold coordinated ruthenium complex, which may also be bridged to form a dimer or trimer. The oxidation state of the ruthenium is preferably 0, +2 or +3. Accordingly, the Ru precursor complex (IV) comprises neutral and/or anionic ligands and, if necessary, one or more non-coordinating anions to achieve the overall charge of "0". In many cases it is not necessary that the Ru precursor complex (IV) already comprises the ligands X and Y and the non-coordinating anion Y of the desired ruthenium complexes (I). The ligands X and Y and the non-coordinating anion Y may also in many cases be added separately to the synthesis. In order to keep the synthetic expense low, readily accessible or readily available complexes are advantageously used as Ru precursor complexes (IV). Such complexes are well known to those skilled in the art. The person skilled in the art is also familiar with the exchange of ligands on ruthenium-containing complexes.

As neutral ligands in the Ru precursor complex (IV), in principle all neutral ligands that are already described under the ligand X are suitable, although two ligands X may of course also be bonded to each other to form a bidentate ligand in the Ru precursor complex (IV). In addition, other neutral ligands not mentioned under X are also possible. Examples here include benzene and p-cymene. Preferred neutral ligands in the Ru precursor complex (IV) include triphenylphosphine, CO and cycloocta-1,5-diene.

As anionic ligands in the Ru precursor complex (IV), in principle all anionic ligands that are already described under the ligand Y are suitable, although the anionic ligand Y in the Ru precursor complex (IV) may of course also be bidentate. In addition, other anionic ligands not mentioned under Y are also possible. An example here is methylallyl.

Preferred anionic ligands in the Ru precursor complex (IV) include Cl—, acetylacetonato and methylallyl.

The reaction of the Ru precursor complex (IV) with the ligand L is typically carried out at a Ru/L molar ratio from 0.8 to 20, preferably from 0.9 to 10 and particularly preferably from 0.9 to 1.1. In order to achieve the highest possible degree of conversion, it is advantageous to use a Ru precursor complex (IV) with only monodentate and bidentate ligands in order to utilize the complexing effect of the tridentate ligand L. The reaction is usually carried out anhydrously, but in the presence of a solvent and under a protective gas atmosphere. Suitable solvents include, for example, aliphatic alcohols such as methanol, ethanol or isopropanol and aromatic hydrocarbons such as toluene or xylenes. In general, ruthenium in the Ru precursor complex (IV) has the same oxidation state as in the subsequent ruthenium complex (I), and thus preferably the oxidation state +2 or +3.

The ruthenium complex (I) may be isolated from the reaction mixture obtained, for example by precipitation or crystallization.

To carry out the hydrogenation according to the invention, however, it is generally not necessary to first isolate the ruthenium complex (I) after its preparation. Rather, it is advantageous in the sense of a simplified procedure to prepare the ruthenium complex (I) as described above from a Ru precursor complex (IV) and the ligand L in the presence of a solvent and to carry out the hydrogenation according to the invention directly in the reaction mixture obtained.

The esters to be used in the method according to the invention can be of a diverse nature. Thus, in principle, linear or branched, non-cyclic or cyclic, saturated or unsaturated, aliphatic, aromatic or araliphatic esters, that are unsubstituted or interrupted by heteroatoms or functional groups, of different molar masses from low to high molecular weight may be used.

The ester used is preferably an ester of the general formula (III)

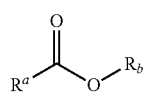
(III)

in which the radicals $R^a$ and $R^b$ are each independently a carbon-containing organic, linear or branched, non-cyclic or cyclic, saturated or unsaturated, aliphatic, aromatic or araliphatic radical which is unsubstituted or interrupted or substituted by heteroatoms or functional groups and has a molar mass of 15 to 10 000 g/mol, it also being possible for the two radicals $R^a$ and $R^b$ to be bonded to each other.

In the case of branched radicals $R^a$ and $R^b$, these may be branched one or more times. Likewise, in the case of cyclic radicals, these may be monocyclic or multi-cyclic. Likewise, in the case of unsaturated radicals, these may be mono- or polyunsaturated, both double bonds and triple bonds being possible here. Heteroatoms are to be understood as atoms that are neither carbon nor hydrogen. Preferred examples of heteroatoms include oxygen, nitrogen, sulfur, phosphorus, fluorine, chlorine, bromine and iodine, and particularly preferred examples are oxygen, nitrogen, fluorine, chlorine and bromine.

Functional groups are another description of groups comprising at least one heteroatom. For example, a hydrocarbon chain interrupted by —O— can be considered both as a hydrocarbon chain interrupted by an oxygen heteroatom and as a hydrocarbon chain interrupted by an ether group. Other non-limiting examples include amino groups (NH$_2$, —NH—, —N<), aldehyde groups (—CHO), carboxyl groups (—COOH), amide groups (CONH$_2$, —CONH—, —CON<), nitrile groups (—CN), isonitrile groups (—NC), nitro groups (NO$_2$), sulfonic acid groups (—SO$_3$), keto groups (>CO), imino groups (>CNH, >CN—), ester groups (—CO—O—), anhydride groups (—CO—O—CO—) and imido groups (—CO—NH—CO—, —CO—NR—CO—). Of course, also two or more so-called functional groups may be present. An example here includes fats.

If the radicals $R^a$ and $R^b$ are bonded to each other, these are cyclic esters, which are also referred to as lactones.

The molar masses of the radicals $R^a$ and $R^b$ are generally 15 to 10 000 g/mol, preferably 15 to 5000 g/mol and particularly preferably 15 to 2000 g/mol.

In the method according to the invention, preference is given to using esters having a molar mass of 74 to 20 000 g/mol, particularly preferably 74 to 10 000 g/mol, especially preferably 74 to 5000 g/mol, especially 74 to 2000 g/mol and in particular 74 to 1000 g/mol.

The molecular hydrogen (H$_2$) to be used in the method according to the invention can be supplied either undiluted or diluted with inert gas, for example nitrogen. It is advantageous to supply a hydrogen-containing gas with the highest possible hydrogen content. Preference is given to a hydrogen content of 80% by volume, particularly preferably of 90% by volume, especially preferably of 95% by volume and particularly of 99% by volume.

In a very general embodiment of the method according to the invention, the ruthenium complex (I), the ester to be hydrogenated and hydrogen are fed to a suitable reaction apparatus and the mixture is reacted under the desired reaction conditions.

The reaction apparatus used in the method according to the invention may in principle be any reaction apparatus which are suitable in principle for gas/liquid reactions under the specified temperature and the specified pressure. Suitable standard reactors for gas/liquid and for liquid/liquid reaction systems are described, for example, in K. D. Henkel, "Reactor Types and Their Industrial Applications", in Ullmann's Encyclopedia of Industrial Chemistry, 2005, Wiley-VCH Verlag GmbH & Co. KGaA, DOI: 10.1002/14356007.b04_087, chapter 3.3 "Reactors for gas-liquid reactions". Examples include stirred tank reactors, tubular reactors or bubble column reactors. Pressure-resistant stirred tanks are usually also referred to as autoclaves.

The ruthenium complex (I) can be fed directly to the reaction apparatus in the form of the previously synthesized ruthenium complex (I). However, this requires a previous synthesis with subsequent work-up or isolation and handling under a protective gas atmosphere.

It is much simpler and preferable that the ruthenium complex (I) is formed in situ from a Ru precursor complex (IV) and ligand L (II). In situ means that the ruthenium complex (I) is formed by supplying Ru precursor complex (IV) and ligand L (II) to the reaction apparatus. Advantageously for this purpose, a molar ratio of ligand L (II) to ruthenium of 0.5 to 5, preferably ≥0.8 and particularly preferably ≥1, and preferably ≤3, particularly preferably ≤2 and especially preferably ≤1.5 is used. This in situ variant spares the prior isolation of the ligand (II).

Another, much simpler possibility for the in situ preparation of the ruthenium complex (I) is to form the ruthenium complex (I) without isolation or purification from a Ru precursor complex (IV) and the synthetic units of the ligand L (II). From the synthetic units of ligand L (II), the ligand (II) is first formed, which coordinates to the ruthenium and results in the ruthenium complex (I). It is therefore particularly preferred that the ruthenium complex (I) is formed in situ by reaction (a) of an aldehyde or ketone of the general formula (Va)

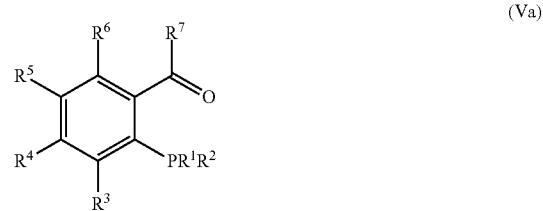
(Va)

with an amine of the general formula (Vb)

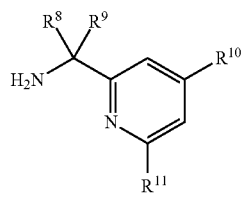

and/or
(b) of an amine of the general formula (VIa)

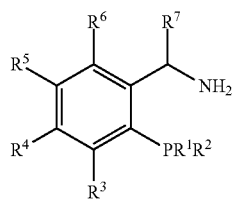

with an aldehyde or a ketone of the general formula (VIb)

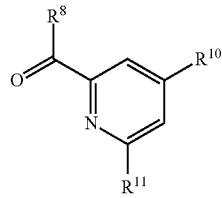

to give the ligand L (II), where the radicals $R^1$ to $R^{11}$ each have the meaning defined above, and subsequent reaction of the ligand L (II) formed, without isolation or purification thereof, with a Ru precursor complex (IV).

The method according to the invention may be carried out in the presence or also in the absence of a solvent. If a solvent is used, this serves, for example, to dissolve the ruthenium complex (I) or a Ru precursor complex (IV) and the ligand L, but also optionally to dissolve the ester to be hydrogenated. Especially in the case of low molecular weight esters, said esters may also function as solvent.

If solvents are used, solvents having more or less pronounced polar properties which are not themselves hydrogenated under the reaction conditions are preferred. Preferred examples include aliphatic alcohols such as methanol, ethanol or isopropanol and aromatic hydrocarbons such as toluene or xylenes. The amount of solvent used can vary widely. However, amounts in the range from 0.1 to 20 g of solvent per g of ester to be hydrogenated, preferably 0.5 to 10 g of solvent per g of ester to be hydrogenated and particularly preferably 1 to 5 g of solvent per g of ester to be hydrogenated, are customary.

The ester to be hydrogenated may be supplied directly in the form of the pure, undiluted ester, but also diluted or dissolved in a solvent. The criteria in which form the ester to be hydrogenated is added are generally often of a purely practical nature, such as, for example, the nature of the ester present and its handling. For example, the aim is for the ester in the reaction mixture to be in liquid form under the reaction conditions.

The molar ratio between the ester to be hydrogenated and the ruthenium complex (I) may vary within a wide range in the method according to the invention. In general, the molar ratio specified in the reaction mixture to be hydrogenated is from 1 to 100 000, preferably from 10 to 25 000, particularly preferably from 100 to 5000 and especially preferably from 500 to 20 000.

The method according to the invention is carried out at a temperature of 50 to 200° C., preferably at ≤170° C. and particularly preferably at ≤150° C. The pressure in this case is 0.1 to 20 MPa abs, preferably ≥1 MPa abs and particularly preferably ≥5 MPa abs, and preferably ≤15 MPa abs and particularly preferably ≤10 MPa abs.

The reaction time or mean residence time in which the reaction mixture is present under the reaction conditions can also vary widely, but is typically in the range from 0.1 to 100 hours, preferably ≥1 hour and particularly preferably ≥2 hours, and preferably ≤80 hours and particularly preferably ≤60 hours.

Furthermore, it has been shown that the hydrogenation according to the invention is generally positively influenced by the presence of a base and, as a result, significantly higher conversions are ultimately made possible. Therefore, in most cases it is advantageous to carry out the hydrogenation in the presence of a base. In exceptional cases, in which, for example, the starting material is base-labile or where secondary reactions occur with base under the reaction conditions, a reaction regime may be more advantageous overall even without a base. In principle, the bases may also be present in the reaction mixture as a solid, but bases which are present in dissolved form in the reaction mixture are preferred. Examples of possible bases include alkoxides, hydroxides, alkali metal and alkaline earth metal carbonates, amides, basic aluminum and silicon compounds and also hydrides. The bases used are particularly preferably alkoxides or amides, preferably sodium methoxide, potassium methoxide, sodium hydroxide, sodium borohydride or sodium hydride, and in particular sodium methoxide and potassium methoxide.

If the method according to the invention is carried out in the presence of a base, this is generally used in excess with respect to the ruthenium complex (I). Preference is given to using a molar ratio of the base to the ruthenium complex (I) of 2 to 1000, preferably of ≥10, particularly preferably of ≥20 and especially preferably of ≥50, and preferably of ≤500 and particularly preferably of ≤250.

The method according to the invention may be carried out continuously, in semi-batch mode, discontinuously, back-mixed in the product as solvent or in a single pass not back-mixed. The ruthenium complex, the ester to be hydrogenated, the hydrogen, optionally the solvent and optionally the base can be fed in simultaneously or separately from one another.

In the discontinuous mode of operation, the ruthenium complex (I) or an Ru precursor complex (IV) and the ligand L (II), the ester to be hydrogenated and optionally solvent and a base are typically initially charged in the reaction apparatus and the desired reaction pressure under the desired reaction conditions is set by mixing by addition of hydrogen. The reaction mixture is then left under the desired reaction conditions for the desired reaction time. Optionally, additional hydrogen is metered in. After the desired reaction time has elapsed, the reaction mixture is cooled or depressurized. The corresponding alcohols can be obtained as reaction products by subsequent work-up. The discontinuous reaction is preferably carried out in a stirred tank.

In the continuous mode of operation, the ruthenium complex (I) or a Ru precursor complex (IV) and the ligand L (II), the ester to be hydrogenated and optionally solvent and a base are continuously fed to the reaction apparatus and a corresponding amount is continuously withdrawn for work-up and isolation of the corresponding alcohol formed.

The continuous reaction is preferably carried out in a stirred tank or a stirred tank cascade.

The hydrogenation product may be separated from the hydrogenation mixture by processes known per se to those skilled in the art such as for example by distillation and/or flash evaporation and the remaining catalyst utilized in the context of further reactions. In the context of the preferred embodiment it is advantageous to eschew addition of solvents and to carry out the reactions cited in the substrate to be converted or the product and optionally in high-boiling by-products as the dissolution medium. Particular preference is given to the continuous reaction regime with reuse or recycling of the homogeneous catalyst.

In the ester hydrogenation according to the invention, a terminal —CH$_2$OH and a terminal —OH group are formed from the —CO—O— ester group. In the case of the esters (III), therefore, the two corresponding alcohols R$^a$—CH$_2$OH and R$^b$—OH are formed corresponding to the following reaction equation.

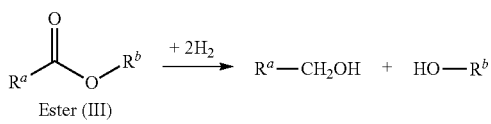

Ester (III)

When using cyclic esters, so-called lactones, the two radicals R$^a$ and R$^b$ are bonded to each other and the corresponding diol is formed.

The method according to the invention enables the preparation of alcohols in high yield and selectivity by homogeneously catalyzed hydrogenation of esters. The hydrogenation may be carried out technically in conventional laboratory equipment for hydrogenation reactions and enables the use of a wide variety of esters as substrates.

The particular advantages of the method according to the invention are based on the specific, tridentate PNN ligands. Due to its tridentate nature, the ligand coordinates tightly to the ruthenium, but has a rather low molar mass compared to many other tridentate ligands of the prior art. For instance, the ligand according to the invention also has only one phosphorus atom, which is advantageous both in terms of production costs and in terms of subsequent disposal. After the formation of the corresponding ruthenium complexes, the ligand according to the invention provides catalysts having high hydrogenation activities. In addition, the ligand according to the invention is also relatively insensitive to oxidation, so that it is also advantageous in terms of handling and has high storage stability.

The particular advantages of the ligand according to the invention, above all, include its ready accessibility and easy possibility of varying the basic structure by replacing hydrogen atoms with various organic radicals. The ligand can generally be prepared from readily available feedstocks by a simple one-pot synthesis. It is generally not necessary to isolate the ligand. Rather, even the synthesis of the ligand and the preparation of the ruthenium complex may be carried out by preparation in an autoclave directly prior to the hydrogenation (without isolation of the intermediates). Ruthenium precursor complexes that are readily accessible and commercially available in large quantities may be used as ruthenium-containing feedstocks.

EXAMPLES

The abbreviations given in Tables 1 to 4 are used in the following examples.

Example 1

Example 1 describes the preparation of the various ligands in the form of Examples 1.1 to 1.8.

Example 1.1 (Preparation of Ligand 1=L1)

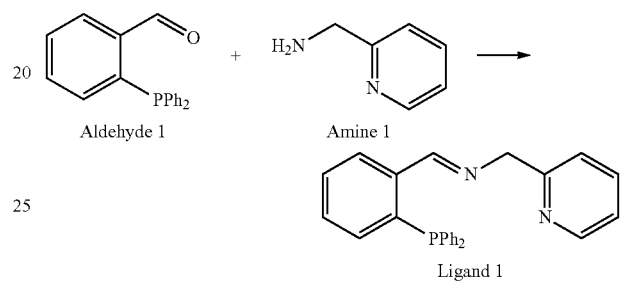

L1 was prepared as described in Rigo et al. in Organometallics 2007, Vol. 26, pages 5636-5642.

$^{31}$P-NMR (203 MHz, CD$_2$Cl$_2$) δ−13.9.

Example 1.2 (Preparation of Ligand 3=L3)

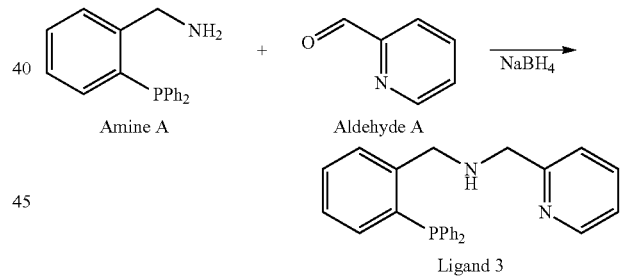

(2-(Diphenylphosphaneyl)phenyl)methanamine (amine A, 1.00 g, 3.43 mmol) was added at room temperature to a solution of picolinaldehyde (aldehyde A, 368 mg, 3.43 mmol) in ethanol (10 mL) and the resulting mixture stirred at room temperature for 2 hours. NaBH$_4$ (208 mg, 5.49 mmol) was added and the mixture was stirred at room temperature for a further 2 hours. Aqueous saturated NaHCO$_3$ solution (15 mL) and CH$_2$Cl$_2$ (25 mL) were then added. After phase separation, the aqueous phase was extracted with CH$_2$Cl$_2$ (2×25 mL). The combined organic phase was dried (Na$_2$SO$_4$) and concentrated in vacuo. The crude product was purified by column chromatography on silica gel (hexane/EtOAc/NEt$_3$, 9:1 to 1:1; a mixture of 10% NEt$_3$ in EtOAc was used) and N-(2-(diphenylphosphaneyl) benzyl)-1-(pyridin-2-yl) methanamine (L3) was obtained as a colorless oil (600 mg, 46% yield).

$^1$H NMR (500 MHz, CD$_2$Cl$_2$) δ 8.48-8.46 (m, 1H), 7.57 (td, J=7.7, 1.8 Hz, 1H), 7.54-7.51 (m, 1H), 7.36-7.30 (m,

7H), 7.28-7.24 (m, 4H), 7.19-7.10 (m, 4H), 6.91 (ddd, J=7.7, 4.5, 1.4 Hz, 1H), 4.02 (d, J=1.7 Hz, 2H), 3.79 (s, 2H). $^{31}$P NMR (203 MHz, CD$_2$Cl$_2$) δ −15.94. HRMS (ESI) C$_{25}$H$_{23}$N$_2$P ([M]$^+$): Calculated: 382.1599. Found: 382.1611.

Example 1.3 (Preparation of Ligand 4=L4)

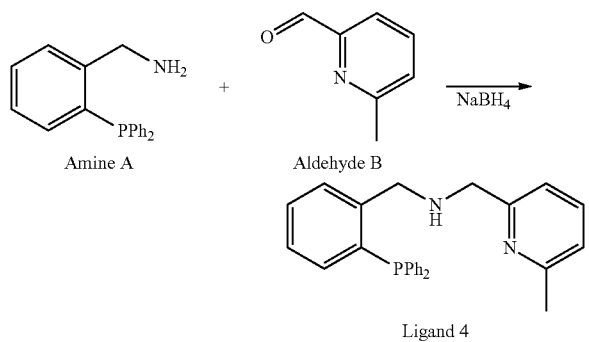

Amine A    Aldehyde B

Ligand 4

(2-(Diphenylphosphaneyl)phenyl)methanamine (amine A, 1.53 g, 5.25 mmol) was added at room temperature to a solution of 6-methylpicolinaldehyde (aldehyde B, 636 mg, 5.25 mmol) in ethanol (20.0 mL) and the resulting mixture stirred at room temperature for 2 hours. NaBH$_4$ (318 mg, 8.41 mmol) was added and the mixture was stirred at room temperature for a further 2 hours. Aqueous saturated NaHCO$_3$ solution (50 mL) and CH$_2$Cl$_2$ (50 mL) were then added. After phase separation, the aqueous phase was extracted with CH$_2$Cl$_2$ (2×25 mL). The combined organic phase was dried (Na$_2$SO$_4$) and concentrated in vacuo. The crude product was purified by column chromatography on silica gel (hexane/EtOAc/NEt$_3$, 9:1 to 6:4; a mixture of 10% NEt$_3$ in EtOAc was used) and N-(2-(diphenylphosphaneyl) benzyl)-1-(6-methylpyridin-2-yl) methanamine (L4) was obtained as a colorless oil (1.23 mg, 3.10 mmol, 59% yield).

$^1$H NMR (500 MHz, CD$_2$Cl$_2$) δ 7.54-7.52 (m, 1H), 7.46 (t, J=7.7 Hz, 1H), 7.36-7.30 (m, 7H), 7.27-7.24 (m, 4H), 7.18-7.15 (m, 2H), 6.98 (d, J=7.7 Hz, 1H), 6.94 (d, J=7.7 Hz, 1H), 6.92-6.89 (m, 1H), 4.01 (s, 2H), 3.74 (s, 2H), 2.47 (s, 3H). $^{31}$P NMR (203 MHz, CD$_2$Cl$_2$) δ −16.31. HRMS (ESI) C$_{26}$H$_2$N$_2$P ([M]$^+$): Calculated: 396.1755. Found: 396.1777.

Example 1.4 (Preparation of Ligand 5=L5)

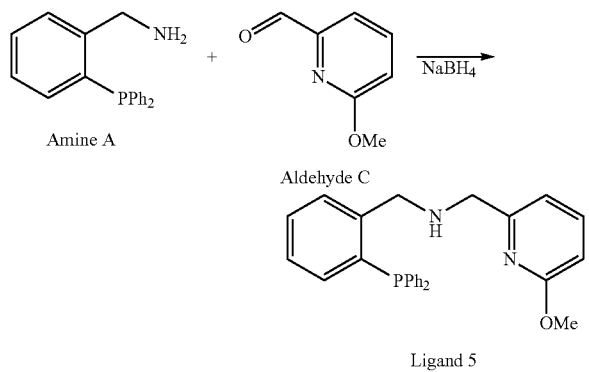

Amine A    Aldehyde C

Ligand 5

(2-(Diphenylphosphaneyl)phenyl)methanamine (amine A, 1.5 g, 5.14 mmol) was added at room temperature to a solution of 6-methoxypicolinaldehyde (aldehyde C, 706 mg, 5.14 mmol) in ethanol (20 mL) and the resulting mixture stirred at room temperature for 2 hours. NaBH$_4$ (311 mg, 8.22 mmol) was added and the mixture was stirred at room temperature for a further 2 hours. Aqueous saturated NaHCO$_3$ solution (50 mL) and CH$_2$Cl$_2$ (50 mL) were then added. After phase separation, the aqueous phase was extracted with CH$_2$Cl$_2$ (2×25 mL). The combined organic phase was dried (Na$_2$SO$_4$) and concentrated in vacuo. The crude product was purified by column chromatography on silica gel (hexane/EtOAc/NEt$_3$, 9:1 to 6:4; a mixture of 10% NEt$_3$ in EtOAc was used) and N-(2-(diphenylphosphaneyl) benzyl)-1-(6-methylpyridin-2-yl) methanamine (L5) was obtained as a colorless oil (1.67 mg, 4.06 mmol, 79% yield).

$^1$H NMR (500 MHz, CD$_2$Cl$_2$) δ 7.56-7.51 (m, 1H), 7.46 (dd, J=8.2, 7.2 Hz, 1H), 7.39-7.28 (m, 7H), 7.27-7.22 (m, 4H), 7.17 (td, J=7.5, 1.4 Hz, 1H), 6.90 (ddd, J=7.7, 4.4, 1.4 Hz, 1H), 6.71 (m, 1H), 6.56 (m, 1H), 4.01 (d, J=1.8 Hz, 2H), 3.86 (s, 3H), 3.69 (s, 2H). $^{31}$P NMR (203 MHz, CD$_2$Cl$_2$) δ −16.25. HRMS (ESI) C$_{26}$H$_{25}$N$_2$P ([M]$^+$): Calculated: 396.1755. Found: 396.1767.

Example 1.5 (Preparation of Ligand 6=L6)

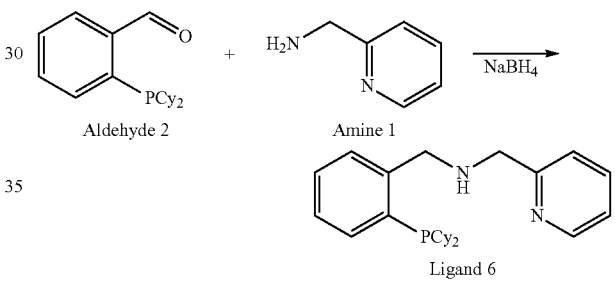

Aldehyde 2    Amine 1

Ligand 6

2-Picolylamine (amine 1, 715 mg, 6.61 mmol) was added at room temperature to a solution of 2-(dicyclohexylphosphaneyl)benzaldehyde (aldehyde 2, 2.00 g, 6.61 mmol) in ethanol (50 mL) and the resulting mixture stirred at room temperature for 2 hours. NaBH4 (401 mg, 10.6 mmol) was added and the mixture was stirred at room temperature for a further 2 hours. Aqueous saturated NaHCO$_3$ solution (100 mL) and CH$_2$Cl$_2$ (75 mL) were then added. After phase separation, the aqueous phase was extracted with CH$_2$Cl$_2$ (2×50 mL). The combined organic phase was dried (Na$_2$SO$_4$) and concentrated in vacuo. The crude product was purified by column chromatography on silica gel (hexane/ EtOAc/NEt$_3$, 9:1 to 3:1; a mixture of 10% NEt$_3$ in EtOAc was used) and N-(2-(dicyclohexylphosphaneyl)benzyl)-1-(pyridin-2-yl) methanamine (L6) was obtained as a colorless oil (1.3 g, 54% yield).

$^1$H NMR (500 MHz, C$_6$D$_6$) δ 8.50-8.49 (m, 1H), 7.51-7.79 (m, 1H), 7.44-7.41 (m, 1H), 7.24-7.22 (m, 1H), 7.18-7.17 (m, 1H), 7.14-7.10 (m, 2H), 6.65-6.62 (m, 1H), 4.31 (d, J=2.1 Hz, 2H), 4.03 (s, 2H), 1.95-1.87 (m, 4H), 1.70-1.53 (m, 9H), 1.30-1.00 (m, 11H). $^{31}$P NMR (203 MHz, CD$_2$Cl$_2$) δ −16.66. HRMS (ESI) C$_{26}$H$_{23}$N$_2$P ([M]$^+$): Calculated: 394.2538. Found: 394.2527.

Example 1.6 (Preparation of Ligand 7=L7)

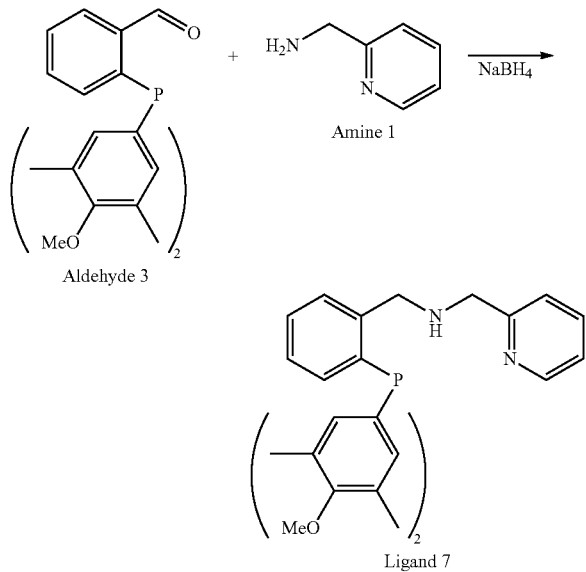

2-Picolylamine (amine 1, 532 mg, 4.92 mmol) was added at room temperature to a solution of 2-(bis(4-methoxy-3,5-dimethylphenyl)phosphaneyl)benzaldehyde (aldehyde 3, 2.00 g, 4.92 mmol) in ethanol (50 mL) and the resulting mixture stirred at room temperature for 2 hours. NaBH$_4$ (300 mg, 7.88 mmol) was added and the mixture was stirred at room temperature for a further 2 h. Aqueous saturated NaHCO$_3$ solution (50 mL) and CH$_2$Cl$_2$ (50 mL) were then added. After phase separation, the aqueous phase was extracted with CH$_2$Cl$_2$ (2×25 mL). The combined organic phase was dried (Na$_2$SO$_4$) and concentrated in vacuo. The crude product was purified by column chromatography on silica gel (hexane/EtOAc/NEt$_3$, 9:1 to 6:4; a mixture of 10% NEt$_3$ in EtOAc was used) and N-(2-(bis(4-methoxy-3,5-dimethylphenyl)phosphaneyl)benzyl)-1-(pyridin-2-yl)methanamine (L7) was obtained as a colorless oil (1.20 g, 50% yield).

$^1$H NMR (500 MHz, C$_6$D$_6$) δ 8.45-8.44 (m, 1H), 7.63-7.60 (m 1H), 7.40 (ddd, J=7.6, 4.4, 1.4 Hz, 1H), 7.27 (s, 2H), 7.25 (s, 2H), 7.18-7.17 (m, 1H), 7.09-7.05 (m, 2H), 7.00-6.98 (m, 1H), 6.63-6.60 (m, 1H), 4.26 (d, J=1.9 Hz, 2H), 3.89 (s, 2H), 3.89 (s, 2H), 3.29 (s, 6H), 2.05 (s, 12H). $^{31}$P NMR (203 MHz, CD$_2$Cl$_2$) δ −17.13. HRMS (ESI) C$_{26}$H$_{25}$N$_2$P ([M]$^+$): Calculated: 498.2436. Found: 498.2441.

General Procedures 1-5 for the Hydrogenation
Procedure 1 (Isolated Ligand)

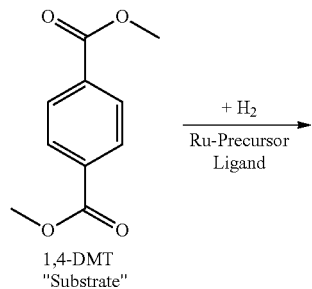

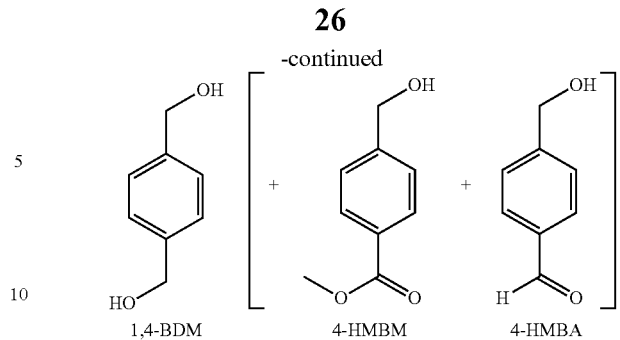

1,4-DMT=methyl 1,4-dimethylterephthalate
1,4-BDM=1,4-benzenedimethanol
4-HMBM=methyl 4-hydroxymethylbenzoate
4-HMBA=4-hydroxymethylbenzaldehyde The selected ligand (as indicated in the respective example), the selected Ru precursor (as indicated in the respective example), methyl 1,4-dimethylterephthalate (as indicated in the respective example) and NaOMe (as indicated in the respective example) were initially charged in a 100 mL autoclave under protective gas and 40 mL of toluene were added. The autoclave was sealed, a hydrogen pressure of 6.0 MPa abs was applied, and heated to the desired reaction temperature at 700 rpm (as indicated in the respective example). After reaching the desired reaction temperature, a hydrogen pressure of 8.0 MPa abs was set. After the desired reaction time had elapsed at the desired reaction temperature, the autoclave was cooled to room temperature, the discharge obtained was concentrated, the yield was optionally determined and the discharge analyzed by GC (dissolution of a sample in dioxane). Optima FFAP column (30 m×0.25 mm/0.5 μm; 15 min at 140° C. then at 20° C./min to 250° C.; flow rate: 2.0 mL/min; hydrogen as carrier gas). Conversion determination by means of GC area %. t$_R$(1,4-BDM)=24.9 min, t$_R$(4-HMBM)=23.0 min, t$_R$(4-HMBA)=22.5 min.

Procedure 2 (without Isolation of the Intermediates of the Ligand L)

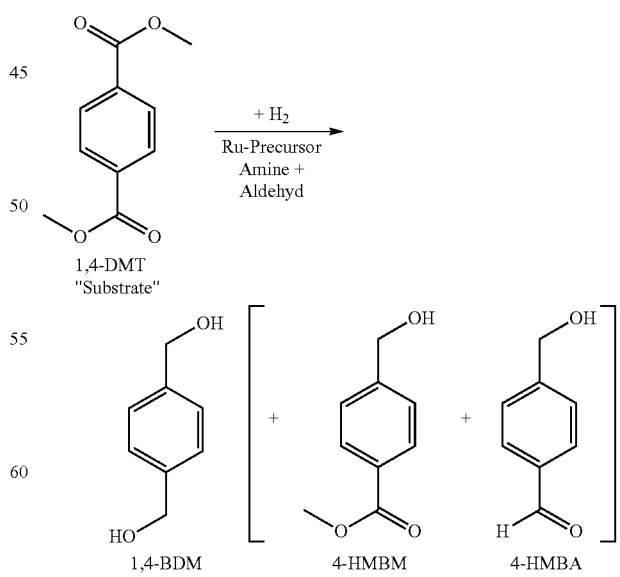

The selected amine (as indicated in the respective example) and the selected aldehyde (as indicated in the respective example) were initially charged in a 100 mL autoclave under protective gas and 20 mL of toluene were added. The autoclave was sealed and heated to 110° C. for 2 hours. The autoclave was then cooled to room temperature and Ru precursor 1 (as indicated in the respective example), methyl 1,4-dimethylterephthalate (as indicated in the respective example) and NaOMe (as indicated in the respective example) were added. 20 mL of toluene were again added, a hydrogen pressure of 6.0 MPa abs was applied and the mixture was heated to 130° C. at 700 rpm. After the internal temperature had reached 130° C., a hydrogen pressure of 8.0 MPa abs was set. After the desired reaction time had elapsed at 130° C., the autoclave was cooled to room temperature, the discharge obtained was concentrated, the yield was optionally determined and the discharge analyzed by GC (dissolution of a sample in dioxane). Optima FFAP column (30 m×0.25 mm/0.5 μm; 15 min at 140° C. then at 20° C./min to 250° C.; flow rate: 2.0 mL/min; hydrogen as carrier gas). Conversion determination by means of GC area %. $t_R$(1,4-BDM)=24.9 min; $t_R$(4-HMBM)=23.0 min, $t_R$(4-HMBA)=22.5 min.

Procedure 3 (Isolated Ligand/Substrate Screening with Base)

The selected ligand (as indicated in the respective example), the selected Ru precursor (as indicated in the respective example), the selected ester (as indicated in the respective example) and KOMe (as indicated in the respective example) were initially charged in a 100 mL autoclave under protective gas and 20 mL of toluene were added. The autoclave was sealed, a hydrogen pressure of 6.0 MPa abs was applied, and heated to the desired reaction temperature at 700 rpm (as indicated in the respective example). After reaching the desired reaction temperature, a hydrogen pressure of 8.0 MPa abs was set. After the desired reaction time had elapsed at the desired reaction temperature, the autoclave was cooled to room temperature and an aliquot of the discharge obtained was analyzed by GC. HP5 column (60 m×0.25 mm/1.0 μm; 5 min at 60° C. then at 20° C./min to 250° C.; flow rate: 2.0 mL/min; helium as carrier gas). The yield by GC was determined using tetrahydropyran (THP) as internal standard. $t_R$(THP)=8.4 min; $t_R$(benzyl alcohol)=13.0 min; $t_R$(methyl benzoate)=13.6 min.

Procedure 4 (Isolated Ligand/Substrate Screening without Base)

Procedure 4 corresponds to procedure 3 with the difference that the reaction was carried out without addition of KOMe.

Procedure 5 (Isolated Ligand/Substrate Screening)

Procedure 5 corresponds to procedure 3 with the difference that the reaction was carried out in THF instead of toluene as solvent and with a different concentration ratio, and NaOMe was used as base.

The selected ligand (as indicated in the respective example), the selected Ru precursor (as indicated in the respective example), the selected ester (as indicated in the respective example) and NaOMe (as indicated in the respective example) were initially charged in a 100 mL autoclave under protective gas and 40 mL of THF were added. The autoclave was sealed, a hydrogen pressure of 6.0 MPa abs was applied, and heated to the desired reaction temperature at 700 rpm (as indicated in the respective example). After reaching the desired reaction temperature, a hydrogen pressure of 8.0 MPa abs was set. After the desired reaction time had elapsed at the desired reaction temperature, the autoclave was cooled to room temperature and an aliquot of the discharge obtained was analyzed by GC. Optima FFAP column (30 m×0.25 mm/0.5 μm; 5 min at 140° C. then at 15° C./min to 250° C.; flow rate: 2.0 mL/min; helium as carrier gas). Conversion determination by means of GC area %.

Example 2

In Example 2, the hydrogenation of methyl 1,4-dimethylterephthalate (1,4-DMT) to 1,4-benzenedimethanol (1,4-BDM) in the presence of a ruthenium complex according to procedure 1 was investigated using various previously synthesized and isolated ligands and various Ru precursors. The data of Examples 2.1 to 2.8 are shown in Table 5.

Using the ligands L1, L3 and L4 and the Ru precursors 1, 2 and 3, very high conversions of 1,4-DMT of up to >98% and very high selectivities for 1,4-BDM of up to >98% were achieved.

Example 3

In Example 3, the hydrogenation of methyl 1,4-dimethylterephthalate (1,4-DMT) to 1,4-benzenedimethanol (1,4-BDM) in the presence of a ruthenium complex according to procedure 2 (without isolating the intermediates) was investigated by preparing various ligands and using various Ru precursors. The data of Examples 3.1 to 3.5 are shown in Table 6.

Using the amines 1, 2 and 3, the aldehyde 1, from which the ligands L1, L2 and L8 are formed, and the Ru precursors 1, 3 and 4, very high conversions of 1,4-DMT of up to >98% and very high selectivities for 1,4-BDM of up to >98% were achieved.

Example 4

In Example 4, the hydrogenation of methyl benzoate to benzyl alcohol in the presence of Ru complex 1 was investigated. Ru complex 1 was used in accordance with the method described in the experimental section of P. Rigo et al., Organometallics 2007, Vol. 26, pages 5636-5642 with the title "Synthesis of trans-[RuCl$_2$(PPh$_3$) (b)] (1)]".

36.7 μmol of Ru complex 1 (30 mg), 36.7 mmol of methyl benzoate and 1.84 mmol of KOMe were initially charged in a 100 mL autoclave under protective gas and 20 mL of toluene were added. The autoclave was sealed, a hydrogen pressure of 6.0 MPa abs applied, and heated to 130° C. at 700 rpm. After reaching 130° C., a hydrogen pressure of 8.0 MPa abs was set. After 16 h at 130° C., the autoclave was cooled to room temperature and an aliquot of the discharge obtained was analyzed by GC. HP5 column (60 m×0.25 mm/1.0 μm; 5 min at 60° C. then at 20° C./min to 250° C.; flow rate: 2.0 mL/min; helium as carrier gas). The yield by GC was determined using tetrahydropyran (THP) as internal standard. $t_R$(THP)=8.4 min; $t_R$(benzyl alcohol)=13.0 min; $t_R$(methyl benzoate)=13.6 min.

The following result was achieved:
Conversion of methyl benzoate: >99%
Selectivity for benzyl alcohol: 99.3%
Selectivity for benzaldehyde: 0.74%

Even when using the previously synthesized ruthenium complex, a very high conversion of >99% and a very high selectivity for benzyl alcohol of >99% were achieved in the hydrogenation of methyl benzoate to benzyl alcohol.

Example 5

In Example 5, the hydrogenation of various esters (as indicated in Table 7) in the presence of a ruthenium complex in accordance with procedures 3, 4 and 5 was investigated using various previously synthesized and isolated ligands and the Ru precursors 2, 3 and 5. Table 7 shows the data of Examples 5.1 to 5.17.

Examples 5.1 to 5.17 show that the method according to the invention may be used widely and, even when using a wide variety of esters, Ru precursors and ligands, enables high conversions and high selectivities for the corresponding alcohols.

Example 6

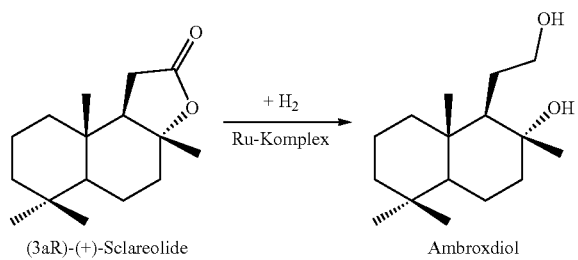

(3aR)-(+)-Sclareolide → Ambroxdiol

In Example 6, the hydrogenation of (3aR)-(+)-sclareolide to ambroxdiol was investigated.

In Examples 6.1 and 6.2, Ru complex 1 (as indicated in Table 8), (3aR)-(+)-sclareolide (as indicated in Table 8) and NaOMe (as indicated in Table 8) were initially charged in a 100 mL autoclave under protective gas and 40 mL of tetrahydrofuran were added. The autoclave was sealed, a hydrogen pressure of 6.0 MPa abs applied, and heated to the desired reaction temperature at 700 rpm (as indicated in Table 8). After reaching the desired reaction temperature, a hydrogen pressure of 8.0 MPa abs was set. After the desired reaction time had elapsed at the desired reaction temperature, the autoclave was cooled to room temperature and the solution obtained was analyzed by GC. Optima FFAP column (30 m×0.25 mm/0.5 μm; 15 min at 140° C. then at 20° C./min to 250° C.; flow rate: 2.0 mL/min; helium as carrier gas). $t_R$(sclareolide)=29.4 min; $t_R$(ambroxdiol)=32.5 min.

In Example 6.3, the hydrogenation of (3aR)-(+)-sclareolide to ambroxdiol in the presence of a ruthenium complex was investigated. The procedure was as in examples 6.1 and 6.2, but in contrast to examples 6.1 and 6.2, the ligand L3 and Ru precursor 3 were used instead of Ru complex 1.

Table 8 shows the data of Examples 6.1 to 6.3.

Example 7

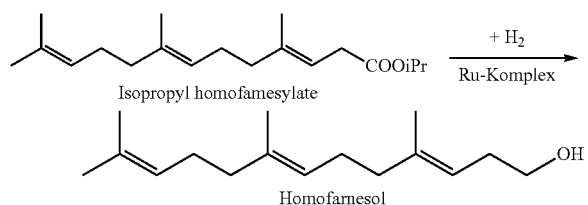

Isopropyl homofarnesylate

Homofarnesol

In Example 7, the hydrogenation of isopropyl homofarnesylate to homofarnesol was investigated.

Ru precursor 5 (as indicated in Table 9) and ligand L3 (as indicated in Table 9) was initially charged in a 100 mL autoclave under protective gas and 30 mL of methanol were added. The autoclave was sealed, a hydrogen pressure of 5.0 MPa abs applied, and heated to 60° C. at 700 rpm for 1.5 hours. The pressure is then briefly released again and NaOMe and isopropyl homofarnesylate dissolved in 10 mL of methanol are added (as indicated in Table 9) under an inert atmosphere. The hydrogen pressure is then set to 5.0 MPa and the autoclave is heated to the desired reaction temperature (as indicated in Table 9) at 700 rpm. After reaching the desired reaction temperature, a hydrogen pressure of 8.0 MPa abs was set. After the specified reaction time had elapsed, the autoclave was cooled to room temperature and the solution obtained was analyzed by GC. VF-23 ms column (60 m×0.25 mm/0.25 μm; 5 min at 50° C. then at 5° C./min to 250° C.; flow rate: 1.0 mL/min; helium as carrier gas). $t_R$(isopropyl homofarnesylate)=34.3 min; $t_R$(homofarnesol, sum of 4 isomers)=35.1, 35.3, 35.7, 35.8 min.

Table 9 shows the data of Example 7.

Example 8

Example 8 shows the reuse of the catalyst after the removal of the product from the first hydrogenation by distillation (catalyst recycling)

36.7 μmol of L3, 12.2 μmol of Ru precursor 5 and 36.7 mmol of methyl benzoate were initially charged in a 100 mL autoclave under protective gas and 20 mL of benzyl alcohol were added. The autoclave was sealed, a hydrogen pressure of 7.0 MPa abs applied, and heated to 130° C. at 700 rpm. After reaching the reaction temperature, a hydrogen pressure of 8.0 MPa abs was set. After a reaction time of 16 hours at 130° C. had elapsed, the autoclave was cooled to room temperature and an aliquot of the discharge obtained was analyzed by GC. HP5 column (60 m×0.25 mm/1.0 μm; 5 min at 60° C. then at 20° C./min to 250° C.; flow rate: 2.0 mL/min; helium as carrier gas). The yield by GC was determined using tetrahydropyran (THP) as internal standard. $t_R$(THP)=8.4 min; $t_R$(benzyl alcohol)=13.0 min; $t_R$(methyl benzoate)=13.6 min. Conversion 99.3%; selectivity 95% benzyl alcohol.

The discharge obtained was concentrated in vacuo and then diluted again with benzyl alcohol to a total volume of 20 mL. The catalyst-containing reaction solution was transferred again to the autoclave under protective gas and another 36.7 mmol of methyl benzoate were added. A hydrogen pressure of 7.0 MPa abs was applied and the autoclave was heated to 130° C. at 700 rpm. After reaching the reaction temperature, a hydrogen pressure of 8.0 MPa abs was set. After a reaction time of 16 hours at 130° C. had elapsed, the autoclave was cooled to room temperature and an aliquot of the discharge obtained was analyzed by GC (method as described above). Conversion 97.8%; selectivity 96% benzyl alcohol.

TABLE 1

Ligand L (Ligand structures shown: Ligand 1 = L1, Ligand 2 = L2, Ligand 3 = L3, Ligand 4 = L4, Ligand 5 = L5, Ligand 6 = L6, Ligand 7 = L7, Ligand 8 = L8, with Ar = 3,5-dimethyl-4-methoxyphenyl)

TABLE 2

Ligand precursors

Amine: Amine 1, Amine 2, Amine 3, Amine A

Aldehyde: Aldehyde 1, Aldehyde 2, Aldehyde 3 (Ar = 3,5-dimethyl-4-methoxyphenyl), Aldehyde A, Aldehyde B, Aldehyde C

TABLE 3

| Ruthenium complex precursor | | | | |
|---|---|---|---|---|
| [Ru(p-cymene)Cl₂]₂ p-cymene = 4-isopropyl-toluene | Ru(Cl)₂(PPh₃)₃ | Ru(acac)₃ acac = acetyl-acetonate | Ru(COD)(methyl-allyl)₂ COD = 1,5-cyclo-octadiene | |
| Ru precursor | Ru precursor 1 | Ru precursor 2 | Ru precursor 3 | Ru precursor 4 |
| Ru₃(CO)₁₂ Ru precursor 5 | | | | |

TABLE 4

Ru complex

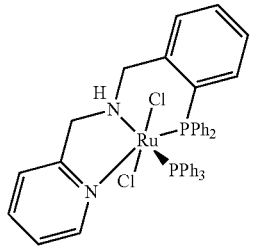

Ru complex 1

TABLE 5

(part 1): Data for examples 2.1 to 2.5 according to procedure 1

| Ex. Amounts used | Reaction conditions | Molar ratio [a] Ligand/Ru [mol/mol] | Molar ratio [a] Substrate/Ru [mol/mol] | Conversion [b] of 1,4-DMT | Selectivity [c] |
|---|---|---|---|---|---|
| 2.1 0.051 mmol L1 from Example 1.1<br>0.026 mmol Ru precursor 1<br>51.5 mmol 1,4-DMT (Substrate)<br>2.5 mmol NaOMe | 130° C.<br>16 h | 1.0 | 1000 | >98% | >98% for 1,4-BDM |
| 2.2 0.051 mmol L3 from Example 1.2<br>0.026 mmol Ru precursor 1<br>51.5 mmol 1,4-DMT (Substrate)<br>2.5 mmol NaOMe | 130° C.<br>16 h | 1.0 | 1000 | >98% | >98% for 1,4-BDM |
| 2.3 0.051 mmol L4 from Example 1.3<br>0.026 mmol Ru precursor 1<br>51.5 mmol 1,4-DMT (Substrate)<br>2.5 mmol NaOMe | 130° C.<br>16 h | 1.0 | 1000 | >98% | 97% for 1,4-BDM |
| 2.4 0.021 mmol L3 from Example 1.2<br>0.005 mmol Ru precursor 1<br>51.5 mmol 1,4-DMT (Substrate)<br>2.5 mmol NaOMe | 130° C.<br>60 h | 2.0 | 5000 | >98% | >98% for 1,4-BDM |
| 2.5 0.010 mmol L3 from Example 1.2<br>0.005 mmol Ru precursor 1<br>51.5 mmol 1,4-DMT (Substrate)<br>2.5 mmol NaOMe | 130° C.<br>60 h | 1.0 | 5000 | >98% | >98% for 1,4-BDM |

[a] rounded figures,
[b] conversion after the end of the reaction,
[c] selectivity after the end of the reaction

TABLE 5

(part 2): Data for examples 2.6 to 2.8 according to procedure 1

| Ex. Amounts used | Reaction conditions | Molar ratio [a] Ligand/Ru [mol/mol] | Molar ratio [a] Substrate/Ru [mol/mol] | Conversion [b] of 1,4-DMT | Selectivity [c] |
|---|---|---|---|---|---|
| 2.6 0.051 mmol L3 from Example 1.2<br>0.051 mmol Ru precursor 2<br>51.5 mmol 1,4-DMT (substrate)<br>2.5 mmol NaOMe | 130° C.<br>16 h | 1.0 | 1000 | >98% | >98% for 1,4-BDM |
| 2.7 0.051 mmol L3 from Example 1.2<br>0.051 mmol Ru precursors<br>51.5 mmol 1,4-DMT (Substrate)<br>2.5 mmol NaOMe | 130° C.<br>16 h | 1.0 | 1000 | >98% | >98% for 1,4-BDM |
| 2.8 0.051 mmol L3 from Example 1.2<br>0.026 mmol Ru precursor 1<br>51.5 mmol 1,4-DMT (Substrate)<br>2.5 mmol KOMe [d] | 130° C.<br>16 h | 1.0 | 1000 | >98% | >98% for 1,4-BDM<br>1% for 4-HMBA |

[a] rounded figures,
[b] conversion after the end of the reaction,
[c] selectivity after the end of the reaction
[d] with KOMe instead of NaOMe

TABLE 6

(part 1): Data for examples 3.1 to 3.4 according to procedure 2

| Ex. | Amounts used | Reaction conditions | Molar ratio [a] Ligand/Ru [mol/mol] | Molar ratio [a] Substrate/Ru [mol/mol] | Conversion [b] of 1,4-DMT | Selectivity [c] |
|---|---|---|---|---|---|---|
| 3.1 | 0.064 mmol aldehyde 1<br>0.064 mmol amine 1<br>0.025 mmol Ru precursor 1<br>51.5 mmol 1,4-DMT (Substrate)<br>2.5 mmol NaOMe | 130° C.<br>16 h | 1.28 | 1000 | >98% | >98% for 1,4-BDM |
| 3.2 | 0.064 mmol aldehyde 1<br>0.064 mmol amine 1<br>0.05 mmol Ru precursor 3<br>51.5 mmol 1,4-DMT (Substrate)<br>2.5 mmol NaOMe | 130° C.<br>16 h | 1.28 | 1000 | >98% | 44% for 1,4-BDM<br>53% for 4-HMBM |
| 3.3 | 0.064 mmol aldehyde 1<br>0.064 mmol amine 1<br>0.05 mmol Ru precursor 4<br>51.5 mmol 1,4-DMT (Substrate)<br>2.5 mmol NaOMe | 130° C.<br>16 h | 1.28 | 1000 | >98% | 97% for 1,4-BDM |
| 3.4 | 0.064 mmol aldehyde 1<br>0.064 mmol amine 2<br>0.025 mmol Ru precursor 1<br>51.5 mmol 1,4-DMT (Substrate)<br>2.5 mmol NaOMe | 130° C.<br>16 h | 1.28 | 1000 | >98% | >98% for 1,4-BDM |

[a] rounded figures,
[b] conversion after the end of the reaction,
[c] selectivity after the end of the reaction

TABLE 6

(part 2): Data for example 3.5 according to procedure 2.

| Ex. | Amounts used | Reaction conditions | Molar ratio [a] Ligand/Ru [mol/mol] | Molar ratio [a] Substrate/Ru [mol/mol] | Conversion [b] of 1,4-DMT | Selectivity [c] |
|---|---|---|---|---|---|---|
| 3.5 | 0.064 mmol aldehyde 1<br>0.064 mmol amine 3<br>0.025 mmol Ru precursor 1<br>51.5 mmol 1,4-DMT (Substrate)<br>2.5 mmol NaOMe | 130° C.<br>16 h | 1.28 | 1000 | >98% | 85% for 1,4-BDM<br>14% for 4-HMBM |

[a] rounded figures,
[b] conversion after the end of the reaction,
[c] selectivity after the end of the reaction

TABLE 7

(part 1): Data for examples 5.1 to 5.4 according to procedure 3

| Ex. | Amounts used | Substrate | Reaction conditions | Alcohol | Conversion [a] of the substrate | Selectivity [b] for the alcohol |
|---|---|---|---|---|---|---|
| 5.1 | Procedure 3<br>36.7 μmol L3 from Example 1.2<br>36.7 μmol Ru precursor 2<br>36.7 mmol of substrate<br>1.84 mmol KOMe | 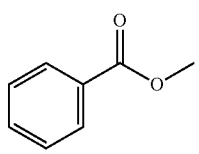<br>Methyl benzoate | 130° C.<br>16 h | Benzyl alcohol | 99% | 99% |

TABLE 7-continued (part 1): Data for examples 5.1 to 5.4 according to procedure 3

| Ex. Amounts used | Substrate | Reaction conditions | Alcohol | Conversion [a] of the substrate | Selectivity [b] for the alcohol |
|---|---|---|---|---|---|
| 5.2 Procedure 3<br>183.5 µmol L4 from Example 1.3<br>183.5 µmol Ru precursor 2<br>36.7 mmol of substrate<br>3.68 mmol KOMe | Methyl benzoate | 130° C.<br>16 h | Benzyl alcohol | 99 | 97 |
| 5.3 Procedure 3<br>183.5 µmol L5 from Example 1.4<br>183.5 µmol Ru precursor 2<br>36.7 mmol of substrate<br>3.68 mmol KOMe | Methyl benzoate | 130° C.<br>16 h | Benzyl alcohol | 99% | 98% |
| 5.4 Procedure 3<br>183.5 µmol L6 from Example 1.5<br>183.5 µmol Ru precursor 2<br>36.7 mmol of substrate<br>3.68 mmol KOMe | Methyl benzoate | 130° C.<br>16 h | Benzyl alcohol | 99% | 97% |

[a] conversion after the end of the reaction,
[b] selectivity after the end of the reaction

TABLE 7

(part 2): Data for examples 5.5 to 5.8 according to procedure 3

| Ex. Amounts used | Substrate | Reaction conditions | Alcohol | Conversion [a] of the substrate | Selectivity [b] for the alcohol |
|---|---|---|---|---|---|
| 5.5 Procedure 3<br>183.5 µmol L7 from Example 1.6<br>183.5 µmol Ru precursor 2<br>36.7 mmol of substrate<br>3.68 mmol KOMe | Methyl benzoate | 130° C.<br>16 h | Benzyl alcohol | 99% | 97% |
| 5.6 Procedure 3<br>36.7 µmol L3 from Example 1.2<br>36.7 µmol Ru precursor 2<br>36.7 µmol of substrate<br>1.84 mmol KOMe | Methyl acetate | 130° C.<br>16 h | Ethanol | 99% | 99% |
| 5.7 Procedure 3<br>73.4 µmol L3 from Example 1.2<br>73.4 µmol Ru precursor 2<br>36.7 mmol of substrate<br>1.84 mmol KOMe | Methyl hexanoate | 130° C.<br>16 h | n-Hexanol | 99% | 97% |

TABLE 7-continued (part 2): Data for examples 5.5 to 5.8 according to procedure 3

| Ex. | Amounts used | Substrate | Reaction conditions | Alcohol | Conversion [a] of the substrate | Selectivity [b] for the alcohol |
|---|---|---|---|---|---|---|
| 5.8 | Procedure 3<br>36.7 μmol L3 from Example 1.2<br>36.7 μmol Ru precursor 2<br>36.7 mmol of substrate<br>1.84 mmol KOMe | Methyl nicotinate | 130° C.<br>16 h | Nicotinyl alcohol | 94% | 94% |

[a] conversion after the end of the reaction,
[b] selectivity after the end oft he reaction

TABLE 7

(part 3): Data for examples 5.9 to 5.11 according to procedures 3 and 4

| Ex. | Amounts used | Substrate | Reaction conditions | Alcohol | Conversion [a] of the substrate | Selectivity [b] for the alcohol |
|---|---|---|---|---|---|---|
| 5.9 | Procedure 3<br>183.5 μmol L3 from Example 1.2<br>183.5 μmol Ru precursor 2<br>36.7 μmol of substrate<br>3.68 mmol KOMe | Methyl 4-(trifluoromethyl) benzoate | 130° C.<br>16 h | 4-(Trifluoromethyl) phenyl) methanol | 99% | 99% |
| 5.10 | Procedure 3<br>183.5 μmol L3 from Example 1.2<br>183.5 μmol Ru precursor 2<br>36.7 μmol of substrate<br>3.68 mmol KOMe | Methyl 4-(methoxy) benzoate | 130° C.<br>16 h | (4-Methoxyphenyl) methanol | 99% | 99% |
| 5.11 | Procedure 4<br>36.7 μmol L3 from example 1.2<br>12.2 μmol Ru precursors<br>36.7 mmol of substrate | Methyl benzoate | 130° C.<br>16 h | Benzyl alcohol | 99% | 98% |

[a] conversion after the end of the reaction,
[b] selectivity after the end oft he reaction

TABLE 7

(part 4): Data for examples 5.12 to 5.14 according to procedure 4

| Ex. | Amounts used | Substrate | Reaction conditions | Alcohol | Conversion [a] of the substrate | Selectivity [b] for the alcohol |
|---|---|---|---|---|---|---|
| 5.12 | Procedure 4<br>46.6 μmol L3 from example 1.2<br>46.6 μmol Ru precursor 3<br>33 mmol of substrate | Ethyl benzoate | 130° C.<br>16 h | Benzyl alcohol | 97% | 99% |

TABLE 7-continued (part 4): Data for examples 5.12 to 5.14 according to procedure 4

| Ex. | Amounts used | Substrate | Reaction conditions | Alcohol | Conversion [a] of the substrate | Selectivity [b] for the alcohol |
|---|---|---|---|---|---|---|
| 5.13 | Procedure 4<br>80.4 μmol L3 from example 1.2<br>26.8 μmol Ru precursors 5<br>28.7 mmol of substrate | Dimethyl adipate | 130° C.<br>16 h | hexane-1,6-diol | 99% | 99% |
| 5.14 | Procedure 4<br>140 μmol L3 from example 1.2<br>46.6 μmol Ru precursors<br>49.9 mmol of substrate | γ-Valerolactone | 130° C.<br>16 h | 1,4-Pentanediol | 97% | 99% |

[a] conversion after the end of the reaction,

[b] selectivity after the end of the reaction

TABLE 7

(part 5): Data for examples 5.15 to 5.17 according to procedure 5

| Ex. | Amounts used | Substrate | Reaction conditions | Alcohol | Conversion [a] of the substrate | Selectivity [b] for the alcohol |
|---|---|---|---|---|---|---|
| 5.15 | Procedure 5<br>38 μmol L3 from example 1.2<br>19 μmol Ru precursor 1<br>38.4 mmol of substrate<br>1.45 mmol NaOMe | Methyl levulinate | 130° C.<br>16 h | 1,4-Pentanediol | >99% | >99% |
| 5.16 | Procedure 5<br>29 μmol L3 from example 1.2<br>15 μmol Ru precursor 1<br>29 mmol of substrate<br>1.45 mmol NaOMe | Butyl levulinate | 130° C.<br>16 h | 1,4-Pentanediol | >99% | 87% 1,4-Pentanediol<br>13% γ-Valerolactone |
| 5.17[c] | Procedure 5<br>35 μmol L3 from example 1.2<br>12 μmol Ru precursor 5<br>34.7 mmol of substrate<br>1.73 mmol NaOMe | Ethyl levulinate | 130° C.<br>16 h | 1,4-Pentanediol | >99% | >99% |

[a] conversion after the end of the reaction,

[b] selectivity after the end of the reaction

[c] Ru precursor 5 and L3 were initially stirred in THF (20 mL) at 60° C. and 50 bar $H_2$ and then the substrate was added in THF (20 mL). The rest of the procedure was then carried out as described in procedure 5.

TABLE 8

Data for Examples 6.1 to 6.3

| Ex. | Amounts used | Reaction conditions | Molar ratio [a] Substrate/Ru [mol/mol] | Conversion [b] of sclareolide | Selectivity [c] (Ambroxdiol) |
|---|---|---|---|---|---|
| 6.1 | 20 μmol Ru complex 1 20 mmol (3aR)-(+)-sclareolide (substrate) 1 mmol NaOMe | 130° C. 16 h | 1000 | 96% | 90% |
| 6.2 | 4 μmol Ru complex 1 20 mmol (3aR)-(+)-sclareolide (substrate) 1 mmol NaOMe | 135° C. 60 h | 5000 | 97% | 88% |
| 6.3 | 8 μmol L3 from Example 1.2 8 μmol Ru precursors 40 mmol (3aR)-(+)-sclareolide (substrate) 2 mmol NaOMe | 135° C. 60 h | 5000 | 84% | 85% |

[a] rounded figures,
[b] conversion after the end of the reaction,
[c] selectivity after the end of the reaction

TABLE 9

Data for example 7

| Ex. | Amounts used | Reaction conditions | Molar ratio [a] Substrate/Ru [mol/mol] | Conversion [b] of the substrate | Selectivity [c] for the alcohol |
|---|---|---|---|---|---|
| 7 | 200 μmol L3 from Example 1.2 66 μmol Ru precursor 5 40 mmol isopropyl homofarnesylate 2 mmol NaOMe | 100° C. 10 h | 200 | 98% | 94% |

[a] rounded figures,
[b] conversion after the end of the reaction,
[c] selectivity after the end of the reaction

The invention claimed is:

1. A method for hydrogenating an ester with molecular hydrogen to give the corresponding alcohols at a temperature of 50 to 200° C. and a pressure of 0.1 to 20 MPa abs in the presence of a five-fold or six-fold coordinated ruthenium complex (I), wherein the ruthenium complex can also be bridged to form a dimer, wherein the ruthenium complex comprises a tridentate ligand L of the general formula (II)

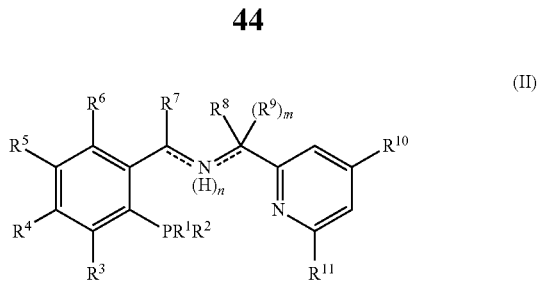

(II)

where
R[1], R[2] are each independently an aliphatic hydrocarbon radical having 1 to 8 carbon atoms, an aromatic hydrocarbon radical having 6 or 10 carbon atoms or an araliphatic hydrocarbon radical having 7 to 12 carbon atoms, where the hydrocarbon radicals specified are unsubstituted or substituted by 1 to 3 methoxy, thiomethoxy or dimethylamino groups, and the two radicals R[1] and R[2] may be bonded to each other to form a 5- to 10-membered ring including the phosphorus atom,
R[3], R[4], R[5], R[6], R[10], R[11] are each independently hydrogen, linear $C_1$ to $C_4$-alkyl, branched $C_3$ to $C_4$-alkyl, methoxy, hydroxyl, trifluoromethyl, nitrile or dialkylamino each independently having 1 to 4 carbon atoms per alkyl group,
R[7], R[8], R[9] are each independently hydrogen, linear $C_1$ to $C_4$-alkyl or branched $C_3$ to $C_4$-alkyl,
n, m are each independently 0 or 1, and
the solid-dashed double lines are a single or double bond, with the proviso that
in the case of n=1, both solid-dashed double lines represent a single bond and m is 1, and
in the case of n=0, one solid-dashed double line represents a single bond and the other solid-dashed double line represents a double bond, wherein in the case of a double bond on the side facing the phenyl ring, m=1, in the case of a double bond on the side facing the pyridyl ring m=0, or both solid-dashed double lines represent a single bond and m is 1.

2. The method according to claim 1, wherein a ligand L (II) is used in which
(i) n and m are in each case 1 and the two solid-dashed double lines represent a single bond, or
(ii) n is 0 and m is 1 and the solid-dashed double line facing the phenyl ring represents a double bond and the solid-dashed double line facing the pyridyl ring represents a single bond,
and
both radicals R[1] and R[2] are phenyl, p-tolyl, 3,5-dimethyl-4-methoxyphenyl, isobutyl or cyclohexyl,
the radicals R[3], R[4] and R[6] are hydrogen,
the radicals R[5] and R[10] are hydrogen, methyl or tert-butyl,
the radical R[11] is hydrogen, methyl or methoxy, and
the radicals R[7], R[8] and R[9] are hydrogen or methyl.

3. The method according to claim 1, wherein the ruthenium complex (I) comprises ruthenium in the oxidation state +2 or +3 and has the general formula (IA)

(IA)

where
X is in each case independently a neutral monodentate ligand, where two ligands X may also be bonded to form a neutral bidentate ligand,
Y is in each case independently an anionic monodentate ligand having a charge of "−1", where Y and X together may also be an anionic bidentate ligand having a charge of "−1", Z is in each case independently a non-coordinating anion having a charge of "−1", where two ligands Z may also be bonded to form a non-coordinating anion having a charge of "−2", a, b and c are each independently 0, 1, 2 or 3, and p is 1 or 2, with the provisos that a+b+c equals 1, 2, 3, 4, 5 or 6, and b and c are determined such that the ruthenium complex (IA) has a total charge of "0".

4. The method according to claim 1, wherein the ruthenium complex (I) is obtained by reacting ligand (II) with a Ru precursor complex (IV).

5. The method according to claim 1, wherein an ester of the general formula (III) is used as ester

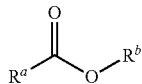
(III)

in which the radicals $R^a$ and $R^b$ are each independently a carbon-containing organic, linear or branched, non-cyclic or cyclic, saturated or unsaturated, aliphatic, aromatic or araliphatic radical which is unsubstituted or interrupted or substituted by heteroatoms or functional groups and has a molar mass of 15 to 10,000 g/mol, it also being possible for the two radicals $R^a$ and $R^b$ to be bonded to each other.

6. The method according to claim 1, wherein the ruthenium complex (I) is formed in situ from a Ru precursor complex (IV) and ligand L (II).

7. The method according to claim 1, wherein the ruthenium complex (I) is formed in situ by reaction (a) of an aldehyde or ketone of the general formula (Va)

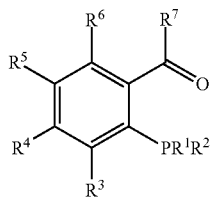
(Va)

with an amine of the general formula (Vb)

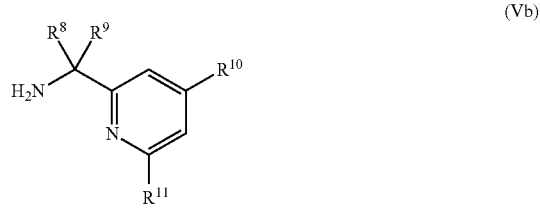
(Vb)

and/or (b) of an amine of the general formula (VIa)

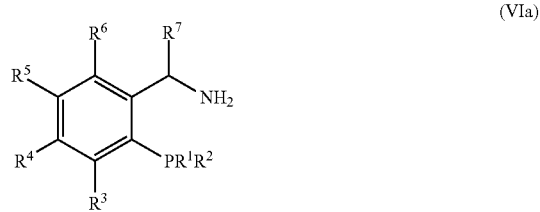
(VIa)

with an aldehyde or a ketone of the general formula (VIb)

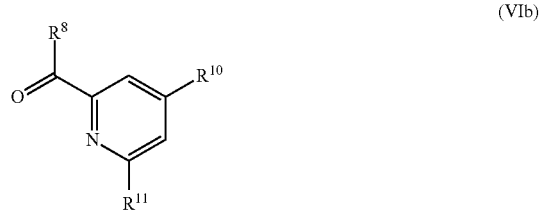
(VIb)

to give the ligand L (II), where the radicals $R^1$ to $R^{11}$ each have the meaning defined above, and subsequent reaction of the ligand L (II) formed, without isolation or purification thereof, with a Ru precursor complex (IV).

8. The method according to claim 1, wherein a molar ratio between the ester and the ruthenium complex (I) of 1 to 100,000 is used.

9. The method according to claim 1, wherein the hydrogenation is carried out in the presence of a base.

10. The method according to claim 9, wherein alkoxides or amides are used as base.

* * * * *